(12) United States Patent
Hensler et al.

(10) Patent No.: US 11,246,974 B2
(45) Date of Patent: *Feb. 15, 2022

(54) COLLECTION AND FILTRATION VIA SUCTION OF BIOLOGICAL MATERIAL DURING SURGICAL PROCEDURE

(71) Applicant: Hensler Surgical Products, LLC, Wilmington, NC (US)

(72) Inventors: Robert Sean Hensler, Wilmington, NC (US); Thomas James Philpott, Charlotte, NC (US); Daniel Lee Bizzell, Charlotte, NC (US); Michael Starkey, Charlotte, NC (US)

(73) Assignee: HENSLER SURGICAL PRODUCTS, LLC, Wilmington, NC (US)

( * ) Notice: Subject to any disclaimer, the term of this patent is extended or adjusted under 35 U.S.C. 154(b) by 441 days.

This patent is subject to a terminal disclaimer.

(21) Appl. No.: 16/532,471

(22) Filed: Aug. 5, 2019

(65) Prior Publication Data

US 2019/0358373 A1 Nov. 28, 2019

Related U.S. Application Data

(63) Continuation of application No. 14/500,964, filed on Sep. 29, 2014, now Pat. No. 10,369,258, which is a
(Continued)

(51) Int. Cl.
*A61M 1/00* (2006.01)
*A61B 17/00* (2006.01)

(52) U.S. Cl.
CPC ............ *A61M 1/79* (2021.05); *A61M 1/0001* (2013.01); *A61M 1/60* (2021.05); *A61B 2017/00969* (2013.01)

(58) Field of Classification Search
CPC ................... A61B 2017/00969; A61F 2/4644
See application file for complete search history.

(56) References Cited

U.S. PATENT DOCUMENTS 2,053,021 A 9/1936 Cassol
2,291,708 A 8/1942 Gluck
(Continued)

FOREIGN PATENT DOCUMENTS

SU 1521464 A1 11/1989
WO 2003073945 A1 9/2003
(Continued)

OTHER PUBLICATIONS

Reexam Order dated May 15, 2020 in U.S. Appl. No. 90/014,484 for U.S. Pat. No. 10,493,183 together with claims from the 183 patent, 14 pages.

*Primary Examiner* — Ariana Zimbouski
(74) *Attorney, Agent, or Firm* — Chad D Tillman; Tillman Wright, PLLC

(57) ABSTRACT

A method for collecting and filtering biological material from blood and other fluids during a surgical procedure includes: attaching a first cover including a suction port and an intake port to a collection trap; attaching a suction source to the suction port; attaching an instrument to the intake port, through which blood and tissue are suctioned and received into the collection trap; filing the collection trap with blood and tissue; removing the collection trap from the first cover; attaching a second cover to the collection trap in place of the first cover, the second cover including a suction port and a plunger, the plunger including a press head having a screen portion permitting blood and other fluids to pass; attaching a suction source to the suction port of the second cover; separating the blood from the tissue by deploying the plunger; and drawing off the blood through the suction port.

20 Claims, 22 Drawing Sheets

Step 7:

Related U.S. Application Data continuation of application No. 13/540,585, filed on Jul. 2, 2012, now Pat. No. 8,845,605, which is a continuation-in-part of application No. 13/429,034, filed on Mar. 23, 2012, now Pat. No. 8,920,393, and a continuation-in-part of application No. PCT/US2012/036414, filed on May 4, 2012, which is a continuation of application No. 13/429,034, filed on Mar. 23, 2012, now Pat. No. 8,920,393.

(60) Provisional application No. 61/483,728, filed on May 8, 2011.

(56) References Cited

U.S. PATENT DOCUMENTS

| | | | |
|---|---|---|---|
| 2,787,308 A | 4/1957 | Popeil | |
| 4,240,570 A | 12/1980 | Brown et al. | |
| 4,261,359 A | 4/1981 | Chein | |
| 4,430,084 A | 2/1984 | Deaton | |
| 4,643,197 A | 2/1987 | Greene et al. | |
| 4,744,955 A | 5/1988 | Shapiro | |
| 4,800,875 A | 1/1989 | Ray | |
| 4,922,902 A | 5/1990 | Wuchinich et al. | |
| 4,974,604 A | 12/1990 | Morris | |
| 5,049,273 A | 9/1991 | Knox | |
| 5,071,409 A | 12/1991 | Rosenberg | |
| 5,279,582 A | 1/1994 | Davison et al. | |
| 5,478,586 A | 12/1995 | Connor | |
| 5,624,418 A | 4/1997 | Shepard | |
| 5,766,134 A | 6/1998 | Lisak | |
| 5,788,976 A | 8/1998 | Bradford | |
| 5,887,510 A | 3/1999 | Porter | |
| 5,954,961 A | 9/1999 | Carchidi | |
| 6,007,496 A | 12/1999 | Brannon | |
| 6,299,763 B1 | 10/2001 | Ashman | |
| 6,347,756 B1 | 2/2002 | Dillard | |
| 6,387,070 B1 | 5/2002 | Marino et al. | |
| 6,494,869 B1 | 12/2002 | Hand | |
| D502,531 S | 3/2005 | Liu | |
| 6,875,220 B2 | 4/2005 | Du et al. | |
| 7,040,218 B1 | 5/2006 | Biolchini, Jr. | |
| 7,204,810 B2 | 4/2007 | Hynes et al. | |
| 7,214,059 B2 | 5/2007 | Takahashi | |
| 7,278,985 B2 | 10/2007 | Agerup | |
| 7,758,556 B2 | 7/2010 | Perez-Cruet et al. | |
| 9,034,044 B2 | 5/2015 | Hensler | |
| 9,636,235 B2 | 5/2017 | Hensler | |
| 9,872,944 B1 | 1/2018 | Willard et al. | |
| 10,232,084 B1 | 3/2019 | Boozari | |
| 2002/0132369 A1 | 9/2002 | Wilkinson | |
| 2004/0167529 A1 | 8/2004 | Papendick et al. | |
| 2005/0055077 A1 | 3/2005 | Marco et al. | |
| 2006/0052760 A1 | 3/2006 | Batzdorf | |
| 2007/0016100 A1 | 1/2007 | Miller | |
| 2007/0028779 A1 | 2/2007 | Pigliacampo et al. | |
| 2007/0203471 A1 | 8/2007 | Anspach et al. | |
| 2007/0225665 A1 | 9/2007 | Perez-Cruet et al. | |
| 2008/0071192 A1 | 3/2008 | Hynes et al. | |
| 2008/0097390 A1 | 4/2008 | Dacquay et al. | |
| 2008/0217264 A1 | 9/2008 | Leach et al. | |
| 2009/0306669 A1 | 12/2009 | Takahaski | |
| 2010/0005979 A1 | 1/2010 | Baccetti | |
| 2010/0255484 A1 | 10/2010 | Halverson et al. | |
| 2010/0275785 A1 | 11/2010 | Weissman et al. | |
| 2011/0056385 A1 | 3/2011 | McLean et al. | |
| 2011/0064611 A1 | 3/2011 | Cioanta et al. | |
| 2012/0129933 A1 | 5/2012 | Wolf | |
| 2012/0220925 A1 | 8/2012 | Seegert et al. | |

FOREIGN PATENT DOCUMENTS

| | | |
|---|---|---|
| WO | 2006023156 A2 | 3/2006 |
| WO | 2012154514 A1 | 11/2012 |

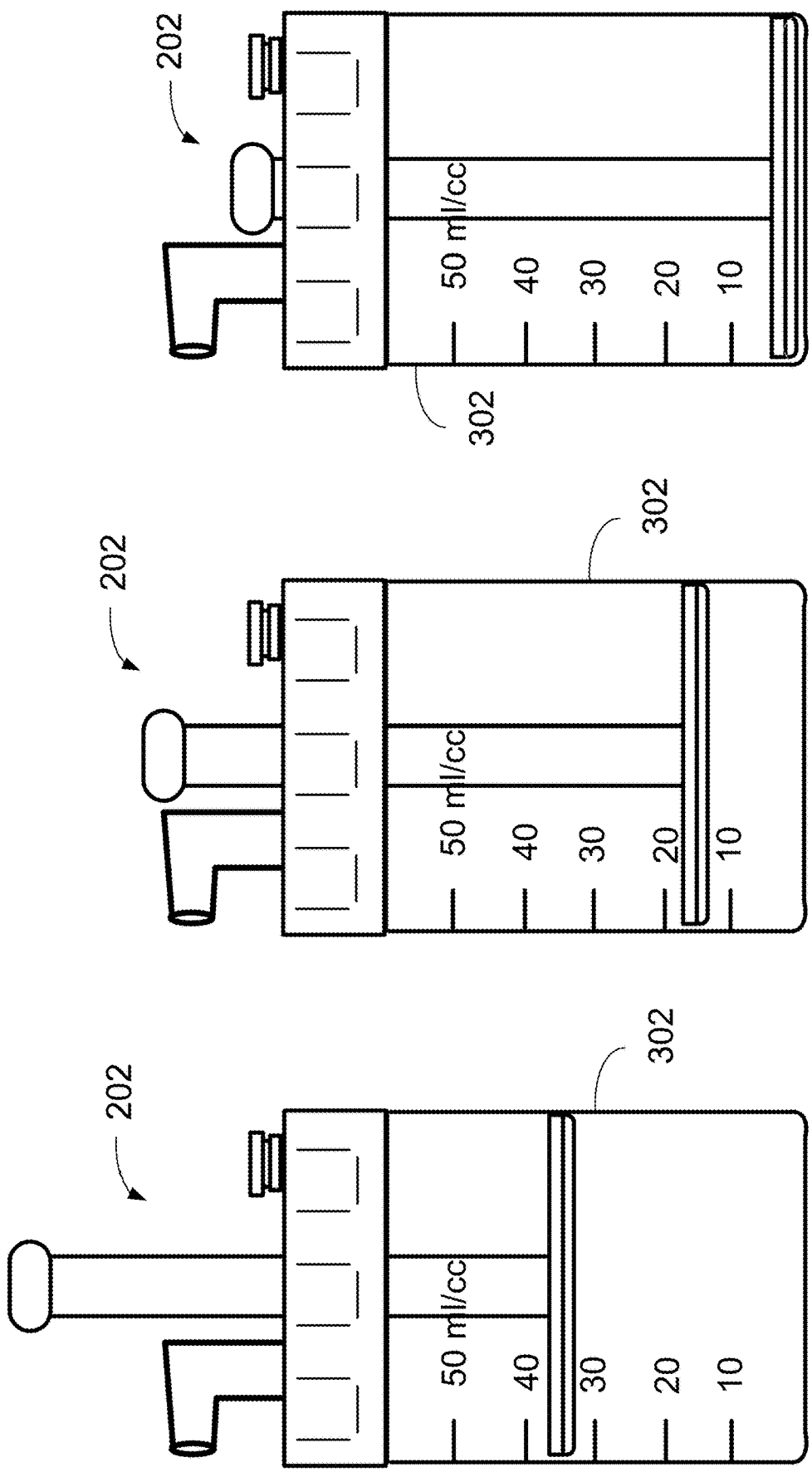

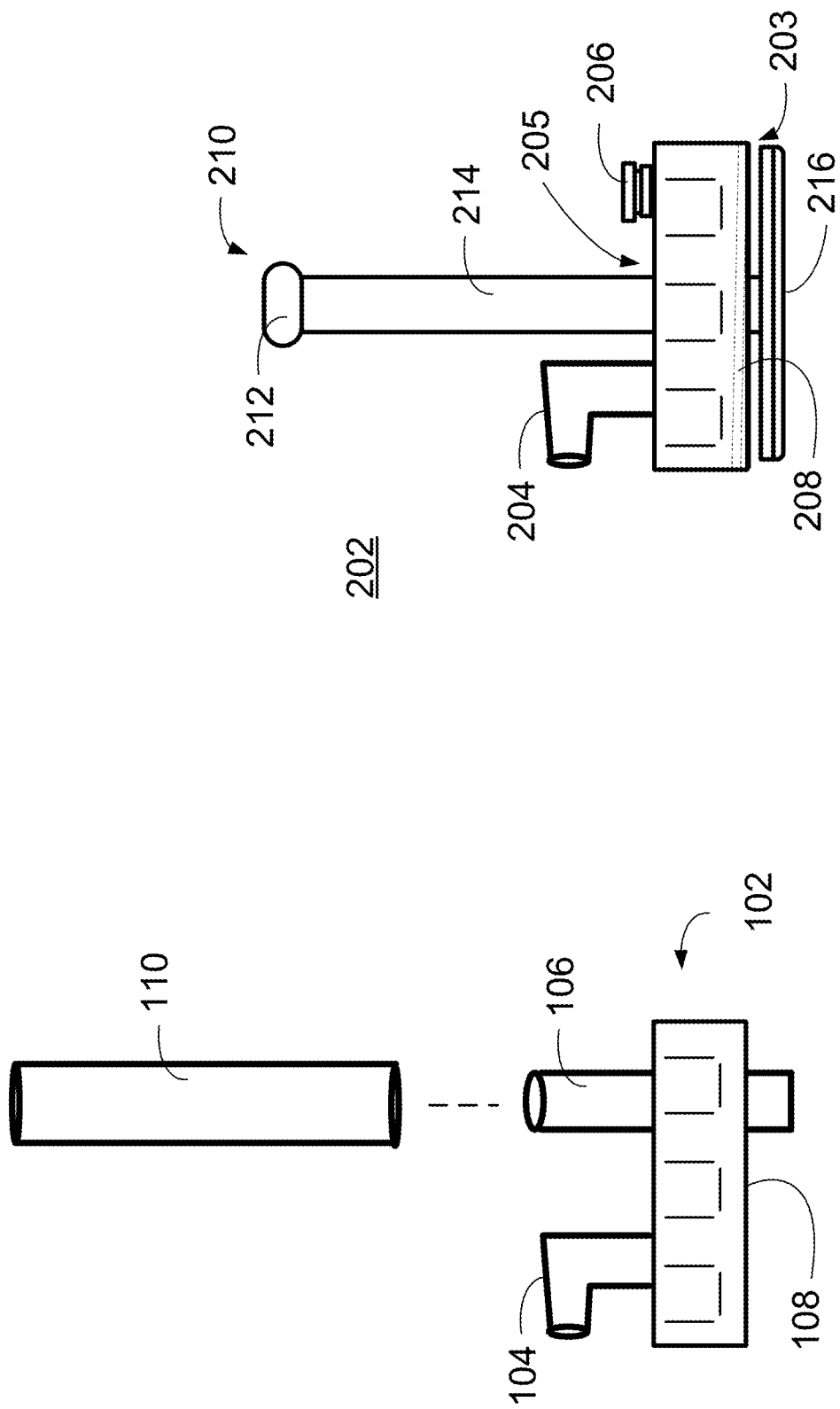

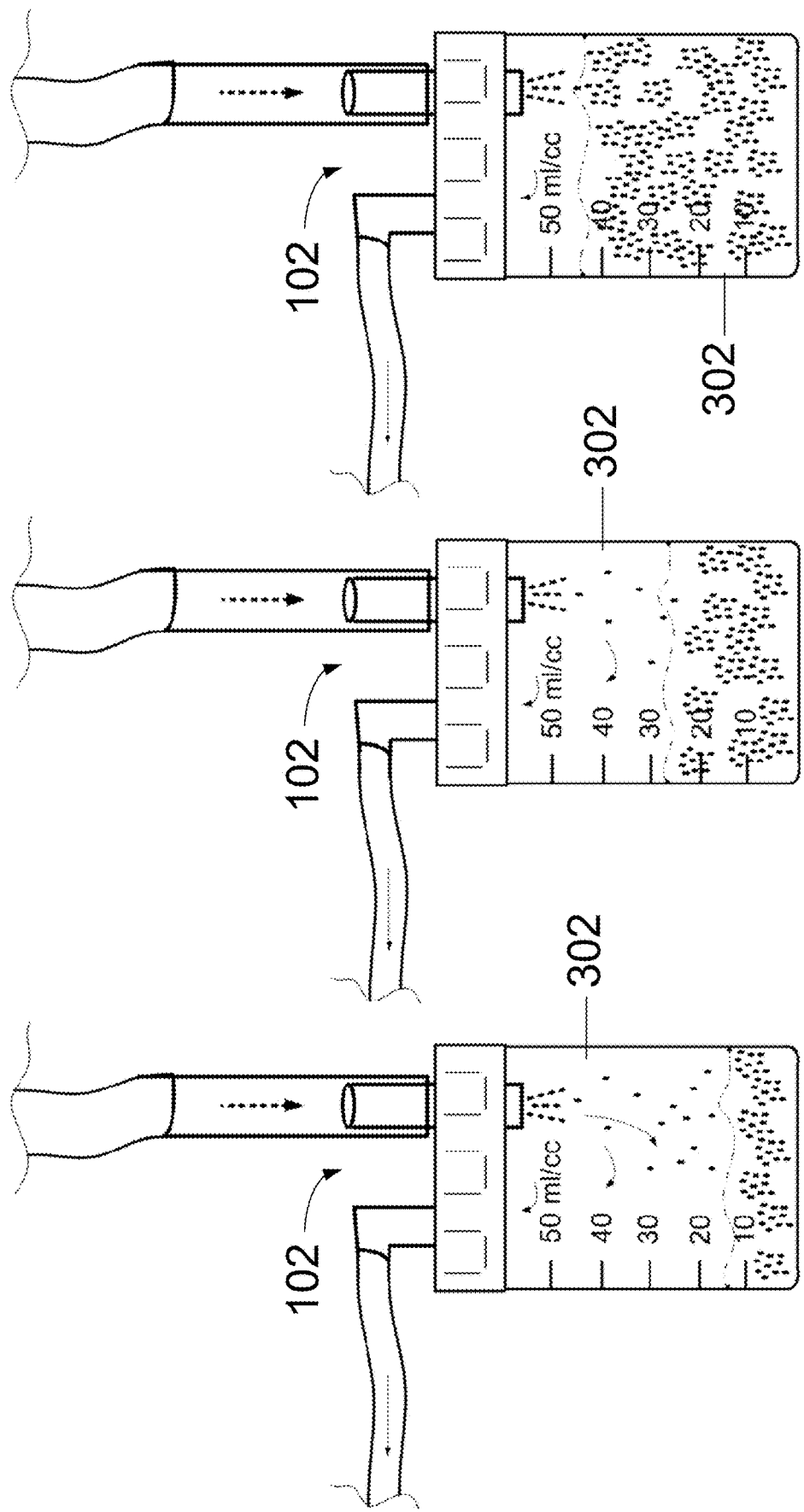

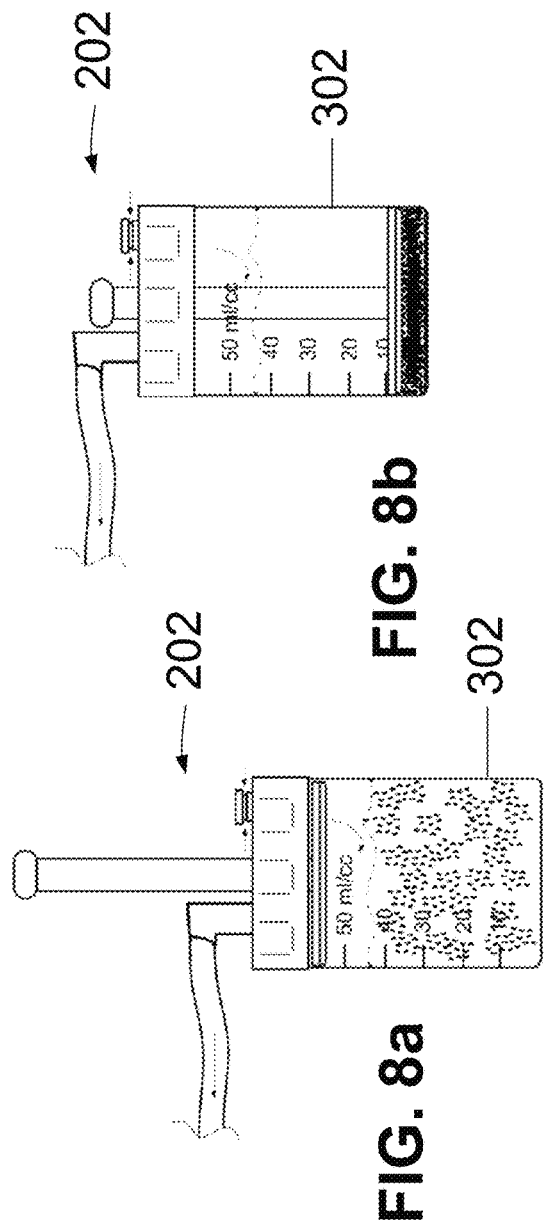
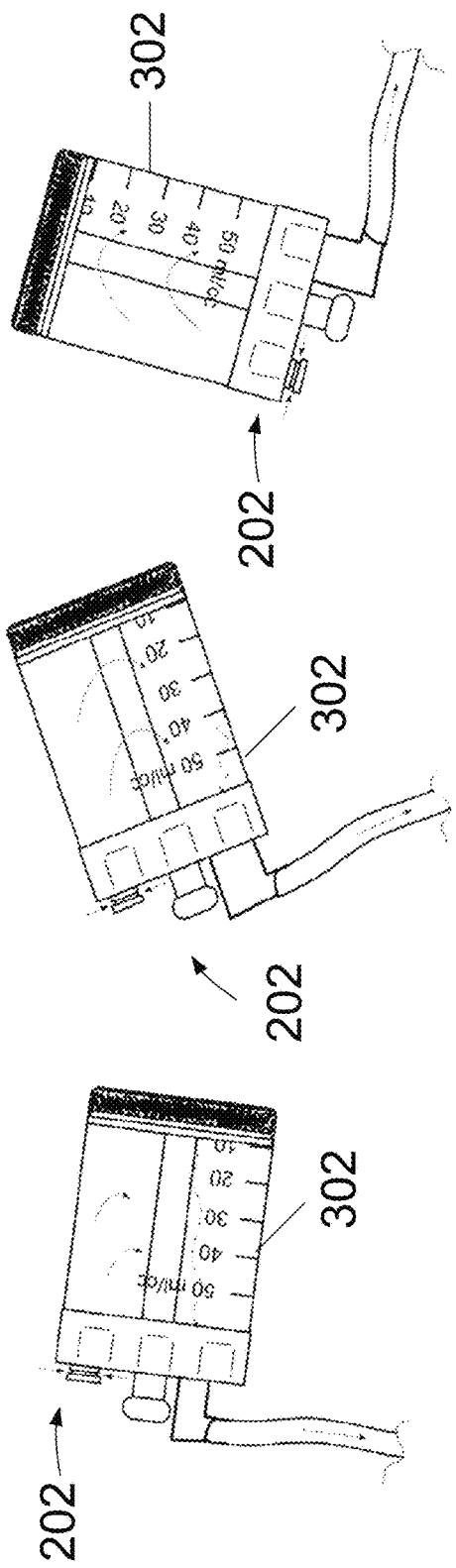
FIG. 8a
FIG. 8b
FIG. 8c
FIG. 8d
FIG. 8e

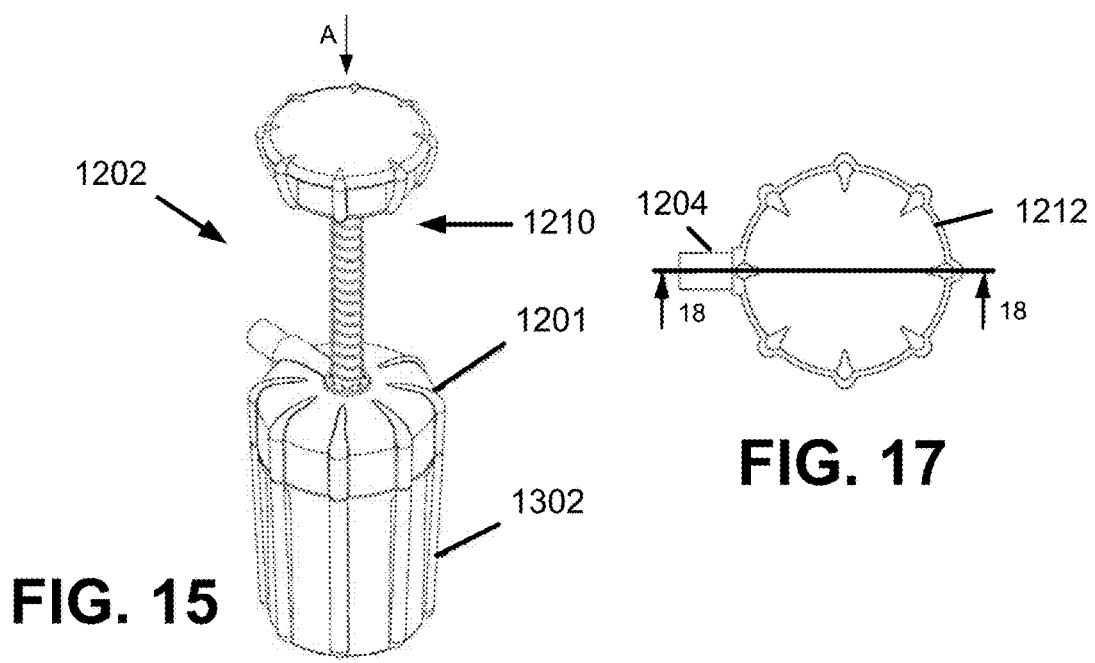
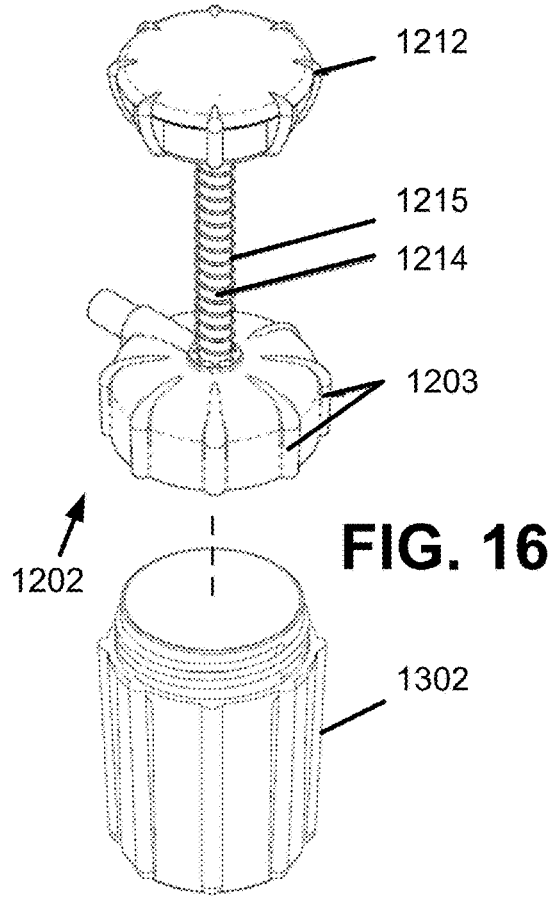
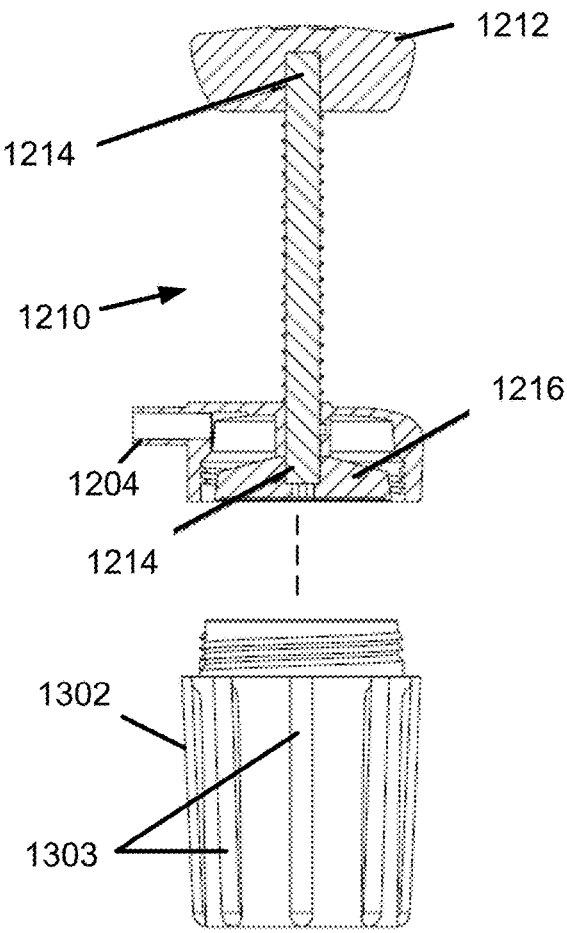

FIG. 19
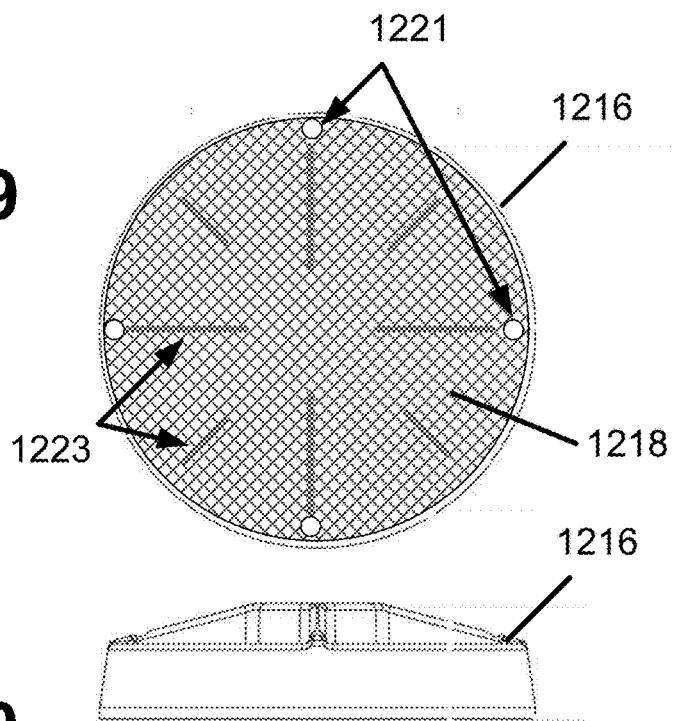
FIG. 20
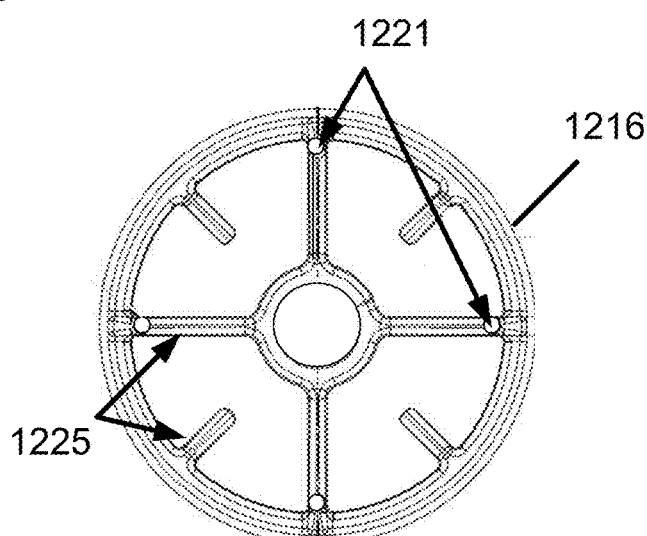
FIG. 21
FIG. 22
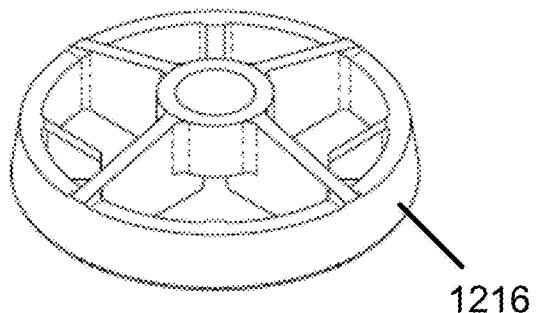

Step 1:

Step 2:

Step 3:

Step 4:

Step 5:

Step 6:

Step 7:

Step 8:

Step 9:

COLLECTION AND FILTRATION VIA SUCTION OF BIOLOGICAL MATERIAL DURING SURGICAL PROCEDURE

The present application is a continuation of, and claims priority under 35 U.S.C. § 120 to, U.S. patent application Ser. No. 14/500,964, filed Sep. 29, 2014, which is a continuation of, and claims priority under 35 U.S.C. § 120 to, U.S. patent application Ser. No. 13/540,585, filed Jul. 2, 2012, which '585 application is a continuation-in-part of, and claims priority under 35 U.S.C. § 120 to, U.S. patent application Ser. No. 13/429,034, filed Mar. 23, 2012, which '034 application is a nonprovisional of, and claims priority under 35 U.S.C. § 119(e) to, U.S. patent application Ser. No. 61/483,728, filed May 8, 2011; and which '585 application is a continuation-in-part of, and claims priority under § 120 to, International patent application serial number PCT/US12/36414, filed May 4, 2012, which international application is a nonprovisional of, and claims priority under § 119(e) to, U.S. patent application Ser. No. 61/483,728, filed May 8, 2011, and which international application is a continuation of, and claims priority under § 120 to, U.S. patent application Ser. No. 13/429,034, filed Mar. 23, 2012, which '034 application is a nonprovisional of, and claims priority under § 119(e) to, U.S. patent application Ser. No. 61/483,728, filed May 8, 2011.

BACKGROUND OF THE INVENTION

The present invention generally relates to collecting material, such as bone or tissue, during a surgical procedure.

Apparatus and methods for collecting bone material are well known. Representative apparatus and methods are disclosed, for example, in the following references: U.S. Pat. Nos. 5,624,418; 5,766,134; 5,954,961; 6,007,496; 6,299,763; 7,204,810; 7,214,059; 7,758,556; USPA Publ. 2007/0016100; USPA Publ. 2007/0203471; USPA Publ. 2007/0225665; USPA Publ. 2008/0071192; USPA Publ. US2009/0306669; and WO 2003/073945. Each of these references is hereby incorporated herein by reference for at least the purposes of disclosing certain contexts and technologies that are pertinent to the present invention.

Generally speaking, operations, such as spinal fusions, require the use of autologous, cancellous bone. The use of this bone is generally preferred; however, the collection methods currently available can be arduous and messy, and some are quite complicated. Indeed, some conventional collection techniques even require the user to pour the contents of blood and bone onto an absorbable pad, such as those sold under the "Telfa" trademark.

In view of known apparatus and methods for collecting bone material, it is believed that one or more needs exist for improvement in apparatus and methods related to collecting bone material during a surgical procedure. This, and other needs, are addressed by one or more aspects of the present invention.

SUMMARY OF THE INVENTION

The present invention includes many aspects and features. Moreover, while many aspects and features relate to, and are described in, the context of collection of bone during surgical procedures, the present invention is not limited to use only in such context, as will become apparent from the following summaries and detailed descriptions of aspects, features, and one or more embodiments of the present invention. For example, the present invention has utility in the collection of tissue other than bone during medical procedures, such as those medical procedures that use an ultrasonic tool for removing tissue.

In a first aspect of the invention, an apparatus for collecting and filtering bone or other tissue from blood includes: (a) a collection trap; (b) a first cover; and (c) a second cover. The first cover and second cover are interchangeably attachable to the collection trap. Additionally, the first cover includes a suction port and an intake port, and the second cover includes a suction port and a plunger. The plunger is configured to separate blood from bone upon depressing of the plunger.

In a related aspect, the collection trap comprises an open-ended cylindrical container; and the first and second covers comprise interchangeable lids that are removably attachable to the open-end of the container in sealing engagement with the container.

In a feature of this aspect, the plunger includes a press head by which bone or other tissue is separated from blood and other fluids. The press head preferably includes a screen through which the blood and other fluids is filtered, and by which bone or other tissue is restrained from passing. Additionally, the screen preferably is retained to the press head by at least a portion of the press head being formed about the screen. The screen is also preferably disk shaped; and the press head preferably includes support members that support the screen at radially extending, elongate areas. Moreover, the screen may be disk shaped and correspond generally to an oval cross-sectional shape of the interior chamber of the container; and the press head may include support members that support the screen only at radially extending, elongate areas, and along one or more outer circumferential edge portions of the screen.

In another feature, the plunger is maintained in a first position, wherein a press head of the plunger is located proximate an underside of the first cover at a mouth of the container. The plunger preferably is lockable in the first position or is spring-biased into the first position.

In another feature, the lids comprise screw-on lids; the container comprises ribs along an exterior surface extending in an axial direction relative to an axis of the container; and each of the first and second covers includes ribs that generally align with the ribs of the container when securely attached to the container, the ribs of the container and the ribs of the lids further providing gripping areas for screwing the lids on and off of the container.

In another feature, the second lid further comprises a vent that is configured to permit air to enter into an interior chamber of the container as a result of the application of suction via the suction port, thereby resulting in a flow for transporting blood and other fluids from the chamber of the container.

In another feature, the plunger comprises a shaft that extends through an opening in a top of the lid of the second cover.

In another feature, the lid preferably defines a passageway that extends from an exterior of the lid to an interior chamber of the container when the lid is attached to the container such that air is permitted to enter into an interior chamber of the container as a result of the application of suction via the suction port of the lid of the second cover, thereby resulting in a flow for transporting blood and other fluids from the interior chamber of the container. The passageway preferably is formed by a recessed area that is defined in an axial extent of a wall defining the opening and that forms a vent when the shaft is received though the opening. The passageway may include elongate top and bottom portions that generally extend in an axial direction and that are connected by an intermediate portion and are offset from each other along a circumferential direction about the opening by the intermediate portion.

In another aspect of the invention, a kit for collecting and filtering bone from blood includes a container in which is contained: (a) a collection trap; (b) a first cover; and (c) a second cover. The first cover and second cover are interchangeably attachable to the collection trap. Additionally, the first cover includes a suction port and an intake port, and the second cover includes a suction port and a plunger. The plunger is configured to separate blood from bone upon depressing of the plunger. The kit also preferably contains a bone scoop; a collection cup; and a length of tubing for attachment to the intake port whereby a suction instrument, such as a Frazier suction tip instrument, may be attached for suctioning of blood and bone.

In another aspect of the invention, a method for collecting and filtering bone from blood includes the steps of: (a) attaching a first cover to a collection trap, the first cover including a suction port and an intake port; (b) attaching a suction source to the suction port; (c) attaching a suction instrument to the intake port, through which blood and bone are received into the collection trap; (d) at least partially filing the collection trap with blood and bone; (e) removing the first cover and attaching to the collection trap a second cover in place of the first cover, the second cover including a plunger, the plunger including a press head having a screen portion permitting blood products to pass there through but generally blocking bone from passing there through; (f) separating the blood from the bone using the plunger; and (g) drawing off the blood from the container. The collection trap may comprise a container; and each cover may comprise a lid that screws onto a mouth of the container.

In a feature, the second cover includes a suction port and the method further includes attaching a suction source to the suction port of the second cover and drawing off the blood from the container through the suction port.

In another aspect, an apparatus for collecting and filtering tissue from blood and other fluids comprises: first and second collection traps; and first and second covers; wherein the first cover comprises a suction port and an intake port; and wherein the second cover comprises a suction port and a plunger.

In a feature of this aspect, each of the first and second collection traps comprises an open-ended cylindrical container; and the first and second covers comprise interchangeable lids that are removably attachable to the open-end of each of the first and second containers in sealing engagement therewith.

In another feature, the plunger includes a press head by which tissue is filtered from blood and other fluids. The press head preferably includes a screen through which blood and other fluids are filtered and by which tissue is restrained from passing. The screen may be retained to the press head by at least a portion of the press head being formed about the screen. In this scenario, the screen preferably is disk shaped; and the press head preferably includes support members that support the screen at radially extending, elongate areas. The screen may also corresponds generally to an oval cross-sectional shape of the interior chamber of the container; and the press head may include support members that support the screen only (i) at radially extending, elongate areas, and (ii) along one or more outer circumferential edge portions of the screen.

Additionally, the plunger preferably is maintained in a first position where at a press head of the plunger is located proximate an underside of the first cover. The plunger may be lockable in the first position; the plunger may be spring-biased into the first position; or both.

In another feature, the lids comprise screw-on lids; each of the containers comprises ribs along an exterior surface extending in an axial direction relative to an axis of the container; and each of the first and second covers includes ribs that generally align with the ribs of each of the containers when securely attached thereto, the ribs of each of the containers and the ribs of the lids further providing gripping areas for screwing the lids on and off of the containers.

In another aspect, a kit for collecting biological material during a surgical procedure includes a container, such as a sterile bag or a box, in which is contained: a first collection trap; a second collection trap; a first cover; and a second cover. The first cover and the second cover are interchangeably attachable to each of the first and the second collection traps. The first cover comprises a suction port and an intake port. The second cover comprises a suction port and a plunger.

In a feature, the kit also includes tubing configured to attach to the suction port of the first cover and an elbow connector configure to attach to the tubing.

In another aspect, a method for collecting and filtering biological material from blood and other fluids during a surgical procedure includes the steps of: (a) attaching a first cover to a collection trap, the first cover including a suction port and an intake port; (b) attaching a suction source to the suction port; (c) attaching an instrument to the intake port, through which instrument blood and tissue are suctioned and received through the intake port into the collection trap; (d) at least partially filing the collection trap with blood and tissue; (e) removing the collection trap from the first cover; (f) attaching a second cover to the collection trap in place of the first cover, the second cover including a suction port and a plunger, the plunger including a press head having a screen portion permitting blood and other fluids to pass there through but generally blocking tissue from passing there through; (g) attaching a suction source to the suction port of the second cover; (h) separating the blood from the tissue by deploying the plunger; and (i) drawing off the blood from the container through the suction port.

In a feature, the method further includes the steps of attaching the first cover to a second collection trap and at least partially filling the second collection trap while performing said steps (f) through (i).

In another feature, the method further includes the step of securing the first cover to a surgical drape on the side of a patient during the surgical procedure, wherein the first cover remains secured to the surgical drape while performing steps (d) through (i).

In another feature, the suction port of the first cover projects outwardly on a side of the first cover, the intake port projects upwardly and orthogonally to a direction of projection of the suction port, and the biological material comprises tissue removed from a patient's body using an ultrasonic device.

In another feature, the intake port of the first cover projects outwardly on a side of the first cover, and the suction port projects upwardly and orthogonally to a direction of projection of the suction port, and the biological material comprises bone removed from a patient's body using a suctioning device.

More aspects and features are disclosed and will become apparent from the followed description of preferred embodiments of the present invention.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more embodiments of the present invention now will be described in detail with reference to the accompanying drawings.

FIG. 1c schematically illustrates the second lid attached to the container, wherein the plunger of the second lid is in a first intermediate position.

FIG. 1d schematically illustrates the second lid attached to the container, wherein the plunger of the second lid is in a second intermediate position.

FIG. 1e schematically illustrates the second lid attached to the container, wherein the plunger of the second lid is in a second position.

FIG. 2 schematically illustrates the first lid of FIG. 1 with the detachable tube that attaches to an intake port of the first lid.

FIG. 3 schematically illustrates the second lid of FIG. 1.

FIGS. 7a-7c schematically illustrate a method of trapping bone and blood products using the container of FIG. 1 with the first lid, in accordance with an embodiment of the present invention.

FIGS. 8a-8e schematically illustrate a method of separating bone from blood products using the container of FIG. 1 with the second lid, in accordance with an embodiment of the present invention.

FIG. 15 schematically illustrates a second lid attached to a container of a bone collection assembly in accordance with another, preferred embodiment of the present invention, wherein a plunger of the second lid is shown in a first position.

FIG. 16 schematically illustrates the detachment of the second lid from the container of FIG. 15.

FIG. 17 schematically illustrates a top plan view of the second lid detached from the container as shown in FIG. 16.

FIG. 18 schematically illustrates a side plan view of the second lid and container of FIG. 17, including a cross-sectional view of the second lid taken along the line 18-18 in FIG. 17.

FIG. 19 schematically illustrates a plan view of the bottom of a press head of the plunger of the second lid of FIG. 18.

FIG. 20 schematically illustrates a side plan view of the press head of FIG. 19.

FIG. 21 schematically illustrates a top plan view of the press head of FIG. 19.

FIG. 22 schematically illustrates a perspective view of the press head of FIG. 19.

FIG. 33b schematically illustrates a front elevational view of the apparatus of FIG. 33a.

FIG. 33c schematically illustrates a side elevational view of the apparatus of FIG. 33a.

FIG. 33d schematically illustrates another side elevational view of the apparatus of FIG. 33a.

FIG. 33e schematically illustrates a rear elevational view of the apparatus of FIG. 33a.

FIG. 33f schematically illustrates a bottom plan view of the apparatus of FIG. 33a.

FIG. 33g schematically illustrates a top plan view of the apparatus of FIG. 33a.

FIG. 34b is another perspective view of the container and cover of FIG. 34a.

DETAILED DESCRIPTION

Figure 1:
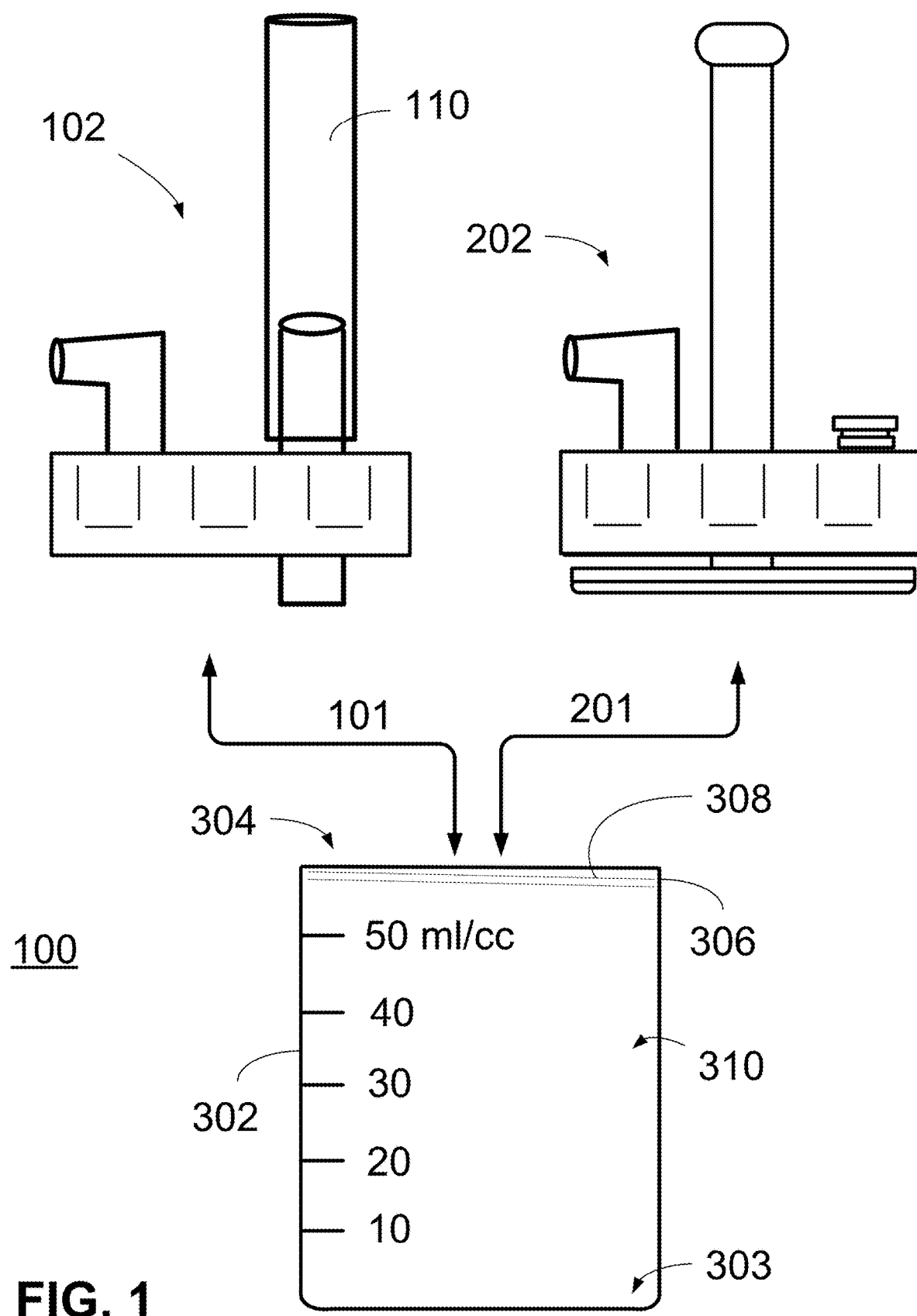
FIG. 1 schematically illustrates a bone collection assembly in accordance with an embodiment of the present invention, including first and second lids and a container.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Components of a Bone Collection Assembly of an Embodiment of the Invention

An exemplary bone collection assembly in accordance with an embodiment of the present invention comprises a collection trap and two interchangeable covers, each of which are configured to attach to the collection trap in covering relation thereto.

With reference to FIG. 1, FIG. 2 and FIG. 3, an exemplary assembly 100 is shown. The assembly 100 includes a collection trap comprises a liquid container 302 having a single, open end comprising a mouth 304 of the container 302; a first cover comprising a first lid 102; and a second cover comprising a second lid 202. The liquid container 302 is illustrated as being a 50 cc container and is suitable for use; however, an 80 cc container is currently preferred with graduations up to 60 cc.

Figure 1A:
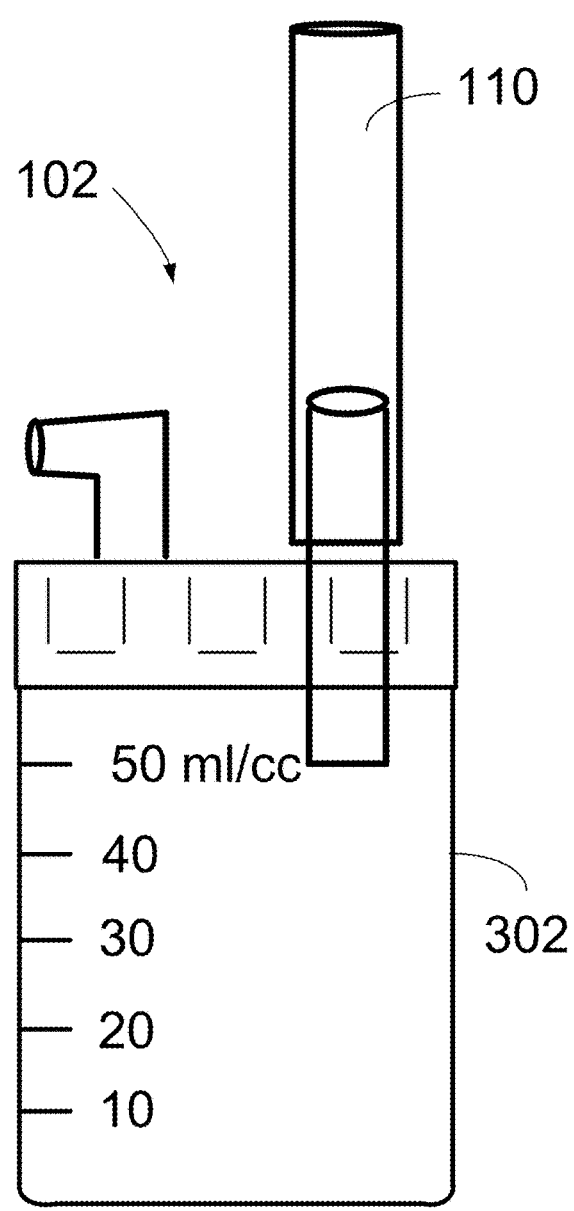
FIG. 1a schematically illustrates the first lid of FIG. 1 attached to the container of FIG. 1.
Figure 1B:
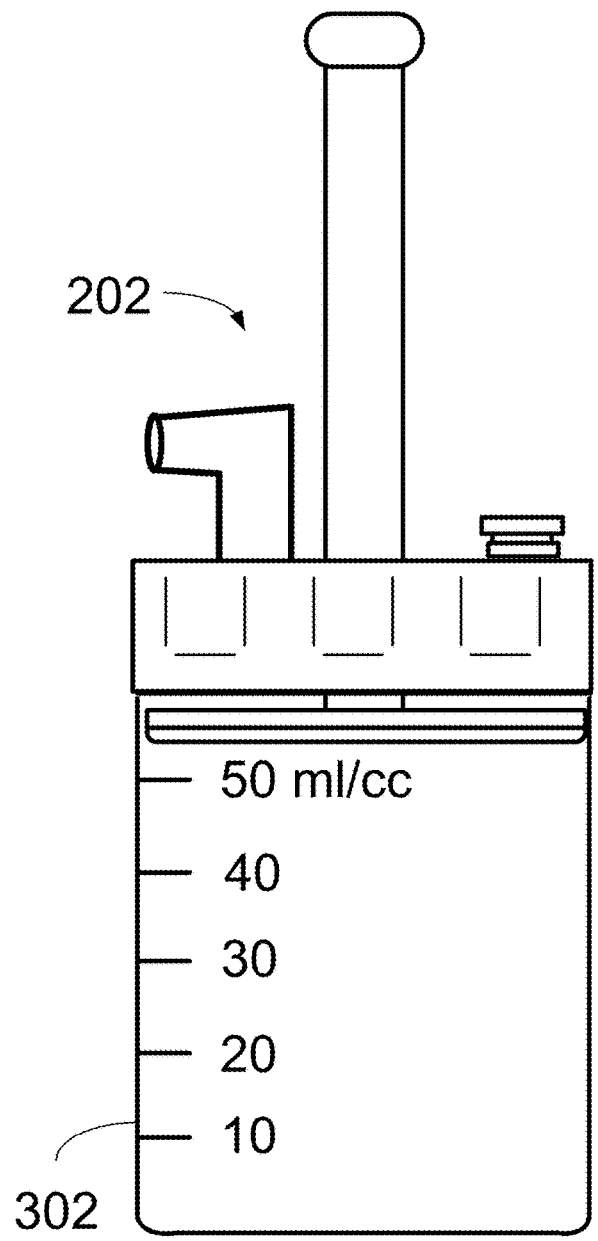
FIG. 1b schematically illustrates the second lid of FIG. 1 attached to the container of FIG. 1, wherein a plunger of the second lid is shown in a first position.

The container 302 includes integral bottom wall and sidewalls that define a continuous, uninterrupted smooth surface, and preferable is cylindrical in shape. The sidewall also is preferably transparent or translucent so that the contents of the container 302 can be viewed, especially as the container 302 fills. A rim 306 surrounding the mouth 304 of the container 302 includes threads 308 for mating engagement with respective threads 108,208 of each of the lids 102,202. In this respect, each lid 102,202 may be interchangeably screwed on top of the container 302 for watertight sealing of the container 302 at the threads, as schematically indicated by the arrows 101,201 in FIG. 1. An illustration of the first lid 102 attached to the container 302 for trapping blood products and bone is shown in FIG. 1a; and an illustration of the second lid 202 attached to the container 302 for separating blood products and bone is shown in FIG. 1b.

With primary reference to FIG. 2, the first lid 102 includes a suction port 104 and an intake port 106. The suction port 104 is configured to receive a tube for application of suction to an interior chamber 310 of the container 302 for holding liquid. The intake port 106 is configured to receive a six-inch tube 110 by which a Frazier suction instrument (not shown) is attachable to the first lid 102. The suction applied to the container 302 via the suction port 104 results in suction being applied via the second port 106 to the Frazier suction instrument, whereby blood products and bone suctioned using the Frazier suction instrument flow through the second port 106 into the collection chamber 310. Moreover, it will be understood that other suction instruments may be used and that the Frazier suction instrument described is merely for purposes of illustration.

Due to the orientation of the container 302 and, in particular, the location of the ports 104,106 in the lid 102 of the container 302, the blood products and bone that are suctioned with the suction instrument are generally trapped and collected within the container 302 by gravity when the container 302 is maintained in a generally upright position with the lid 102 attached to the chamber 310.

With primary reference to FIG. 3, the second lid 202 includes a suction port 204, a vent 206, and a plunger 210. The suction port 204 is similar to that of the first lid 102, and is configured to receive a tube for application of suction to the interior chamber 310 of the container 302 when attached thereto. The vent 206 is configured to permit air to enter into the chamber 310 of the container 302 when attached thereto as a result of the application of the suction via the suction port 204, thereby resulting in an airflow. This airflow is utilized to transport blood products from the chamber 310, as will be described in further detail below.

The plunger 210 itself comprises a handle 212, a shaft 214, and a press head 216. The plunger 210 is able to transition (i.e., is transitionable) between a first, extended position (as shown in FIG. 1b), in which the press head 216 is located proximate a bottom 203 of the second lid 202, and a second depressed position (as shown in FIG. 1e) in which the handle 212 is located proximate a top 205 of the second lid 202 and the press head 216 is located proximate the bottom 303 of the container 302 when the second lid 202 is attached to the container 302. First and second intermediate positions of the plunger 210 between these first and second positions are shown, respectively, in FIG. 1c and FIG. 1d.

Figure 3A:
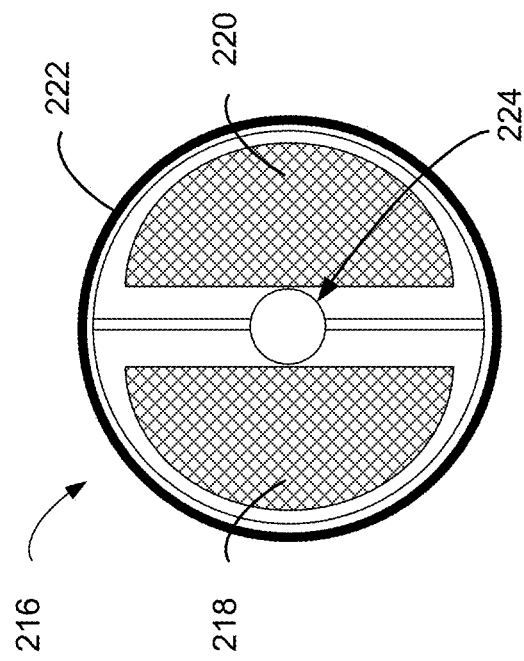
FIG. 3a schematically illustrates a press head of the second lid of FIG. 1.

Furthermore, as shown in FIG. 3a, the press head 216 includes a screen comprising two screen portions 218,220. Each screen portion 218,220 preferably comprises a fine metal screen mesh. The screen is configured to filter bone from the blood products, in that the screen includes openings dimensioned to allow blood products to pass there through, but to generally block autologous, cancellous bone obtained during a surgical procedure from passing therethrough. Consequently, when the second lid 202 is attached to a container 302 that has filled with blood products and bone obtained during a surgical procedure, transitioning of the plunger 210 from the first position to the second position results in the separation of the blood products and the autologous, cancellous bone. The press head 216 also includes a rubber O-ring 222 for sealing engagement with the interior sides of the chamber 310 of the container 302 so that bone does not pass around the press head 216 during transitioning of the plunger 210. The press head 216 attaches to the shaft 214 at 224.

Figure 4:
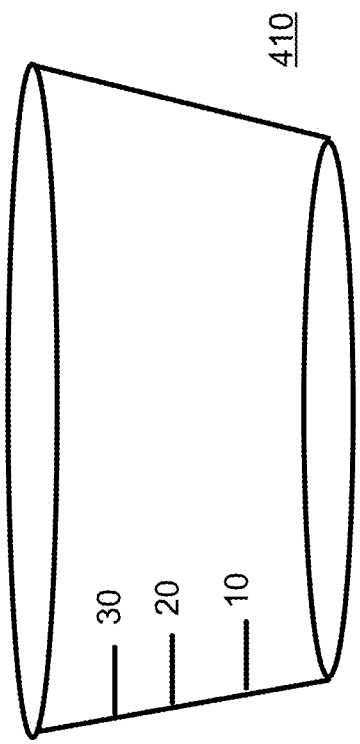
FIG. 4 schematically illustrates a collection cup that comprises part of a bone collection system in accordance with an embodiment of the present invention.
Figure 5:
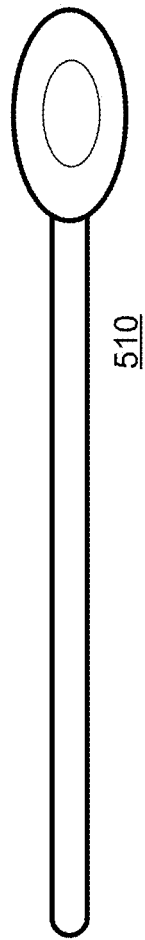
FIG. 5 schematically illustrates a bone spoon that comprises part of a bone collection system in accordance with an embodiment of the present invention.

The bone collection assembly also includes a collection cup, an exemplary embodiment 410 of which is shown in FIG. 4; and a bone scoop, an exemplary embodiment 510 of which is shown in FIG. 5. The bone scoop 510 is used to physically transfer filtered bone retained in the collection trap to the collection cup 410. The collection cup 410 is used to hold the autologous, cancellous bone until needed in a surgical procedure.

The foregoing called-out components of the bone collection assembly 100 preferably are made out of one or more plastic materials, and may be manufactured using injection-molding processes. Exceptions include the screen of the press head, which preferably is made out of a stainless steel woven mesh; the tube, which preferably is made out of silicone; and the O-ring, which preferably is made out of a rubber material.

An Exemplary Commercial Kit

Figure 6:
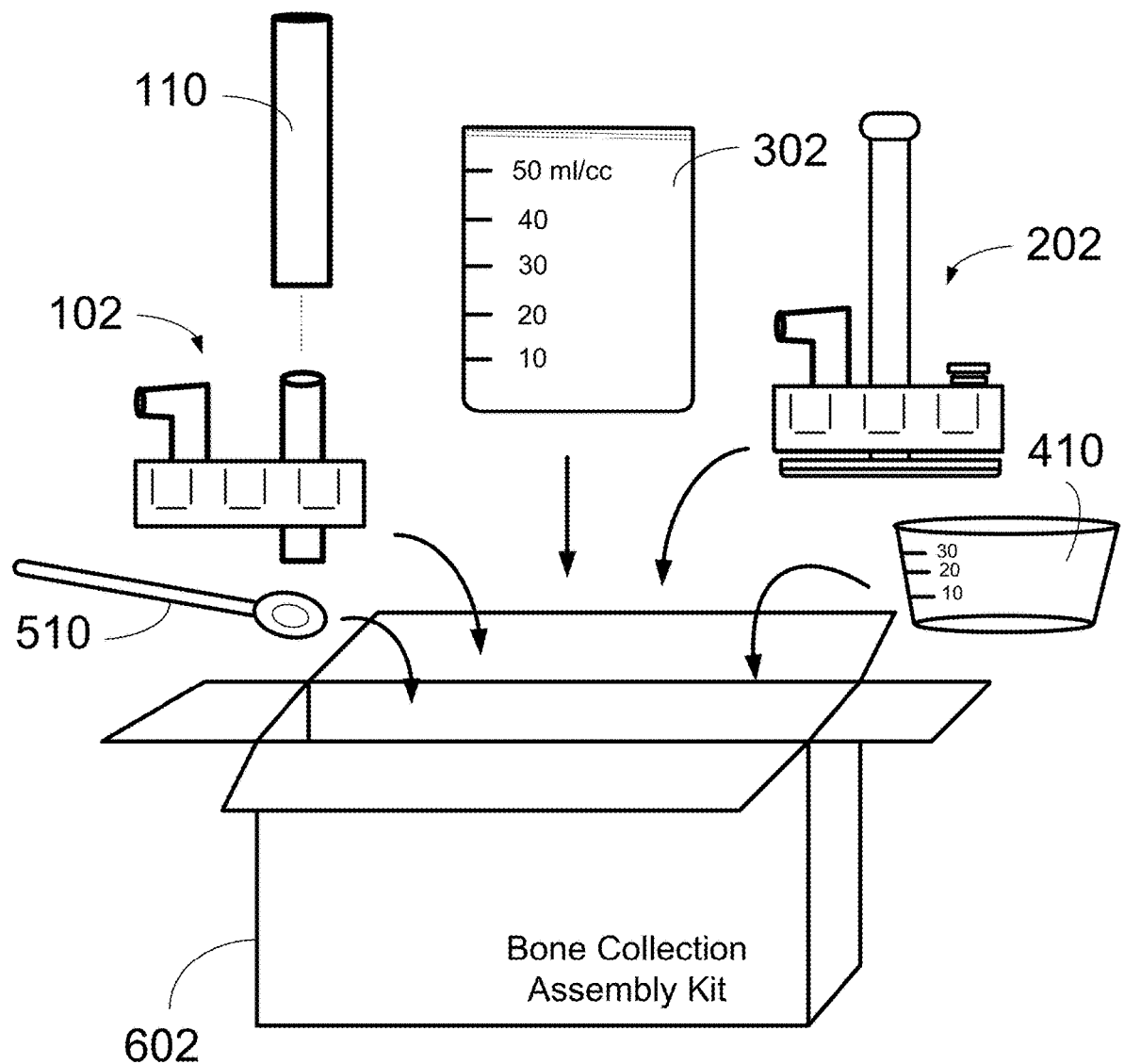
FIG. 6 schematically illustrates a bone collection assembly kit in accordance with an embodiment of the present invention.

Components of an exemplary commercial kit 600 in accordance with the present invention are shown in FIG. 6 and comprises a container 302; a first lid 102; a tube 110; a second lid 202; and a box 602. The kit 600 may also contain a collection cup 410 and a bone scoop 510. The container and collection cup preferably are clear plastic, and the colors of the lids are white. The tube 110 preferably comprises clear, plastic tubing. The tube 110 is attachable to the port 106 of the first lid 102 and may either be separately contained within the box 602 or pre-attached to the second port 106. The bone scoop 510 also preferably is white. The components in the box 602 are preferably packaged in sterile pouches, are opened by sterile technique, and are intended to be placed on a sterile table within an operating environment, such as a mayo table, and opened for use in preparation for, or during, a surgical procedure. Furthermore, while a kit may include only one container within the scope of the invention, the kit may include a second container (not shown) that is identical to the first container whereby bone and blood can be captured during the surgical operation using the first lid and one of the two containers even as bone is being filtered from blood using the second lid and the other container. In a preferred commercial kit, a bone collection assembly represented by FIGS. 15-34 is provided with two identical containers for use, as described below.

Exemplary Use During Surgical Procedure

Once the need arises for collection of bone, a bone collection assembly kit is brought to the surgeon and/or assistant. The box is opened, and a first lid is attached in threading engagement with the container. The suction port of the first lid is then attached to a suction source. A Frazier suction instrument (or other suction instrument) is attached to the open end of the plastic tubing attached to the second port. Both the suction instrument and the suction source are conventionally provided in individual operating rooms and are not part of the kit. Once the blood products and bone approximately fills the container, the suction is removed from the suction port. The first lid is then removed from the container by unscrewing it while keeping the suction instrument attached on the end of the tubing. Leaving the suction instrument attached will facilitate the process of further bone collecting. Accordingly, the lid is placed on the surgical table for quick access later, or if a second container is provided, then the lid is attached to the second container and the suction is reapplied to the suction port for continued bone and blood collection.

The steps of collecting bone and blood products within the container are illustrated in FIGS. 7a-7c.

The second lid then is attached in threading engagement to the filled container. Suction is applied to the suction port on the second lid while keeping the container upright not allowing for any incidental suction of bone products. The user then depresses the plunger until it is fully depressed, thereby compressing the bone and separating the bone from the blood products. The blood then is suctioned away by tilting the container while the bone is maintained under pressure by depression of the plunger. After the blood has been evacuated by the suction, the suction is removed and the plunger is raised and locked—or otherwise maintained—in position. The lid is then removed from the container. The bone within the container is then collected by use of the bone scoop and transferred to the collection cup. Additionally, bone may adhere to the press head. Any bone adhering to the press head also is collected with the bone scoop and transferred to the collection cup. Thereafter, if further bone collecting is desired and a second container is not being used, then the first lid is again reattached to the container and the foregoing steps are repeated for collecting bone and blood.

Figure 9:
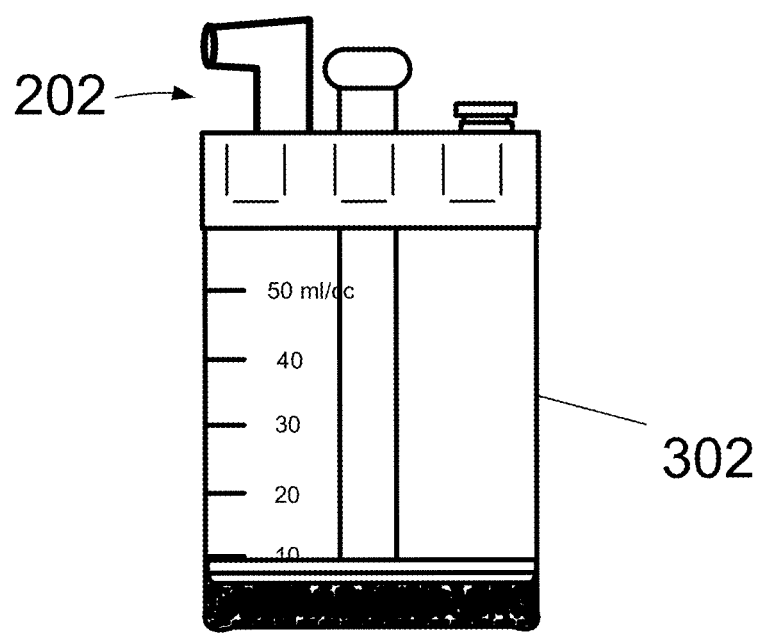
FIG. 9 schematically illustrates bone remaining in the container following the method illustrated in FIGS. 8a-8e.
Figure 10:
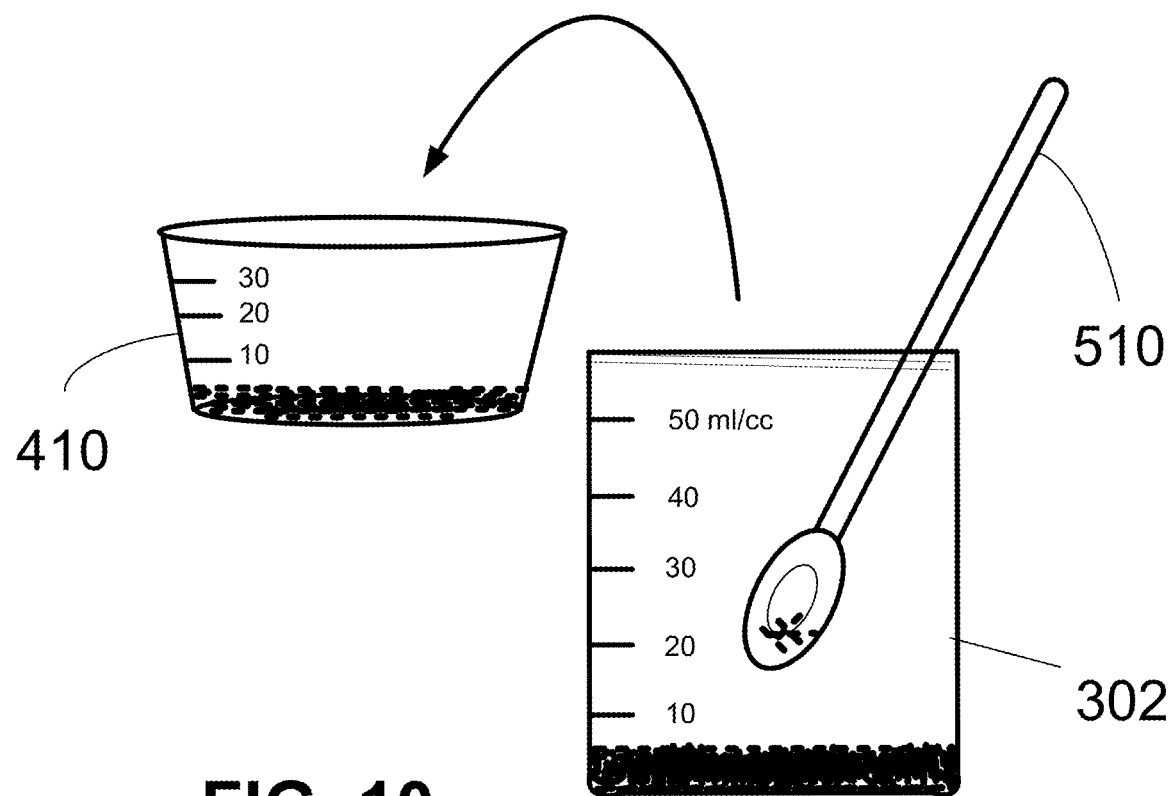
FIG. 10 schematically illustrates the transfer of bone remaining in the container of FIG. 9 using the bone spoon of FIG. 5, in accordance with an embodiment of the present invention.

The separation of bone and blood products within the container are illustrated in FIGS. 8a-8d, and the transfer of the bone from the container to the collection cup is represented by FIGS. 9-10.

Upon completion of the surgical procedure, or if the surgeon is in no further need for bone collection, the bone collection assembly can be discarded by hazmat standards per facility given its disposable design. Indeed, the bone collection assembly preferably is disposable, although in other embodiments it is contemplated that one or more components of the bone collection assembly could be reusable, preferably after autoclaving.

Additional Detail with Regard to the First and Second Lids

Figure 11:
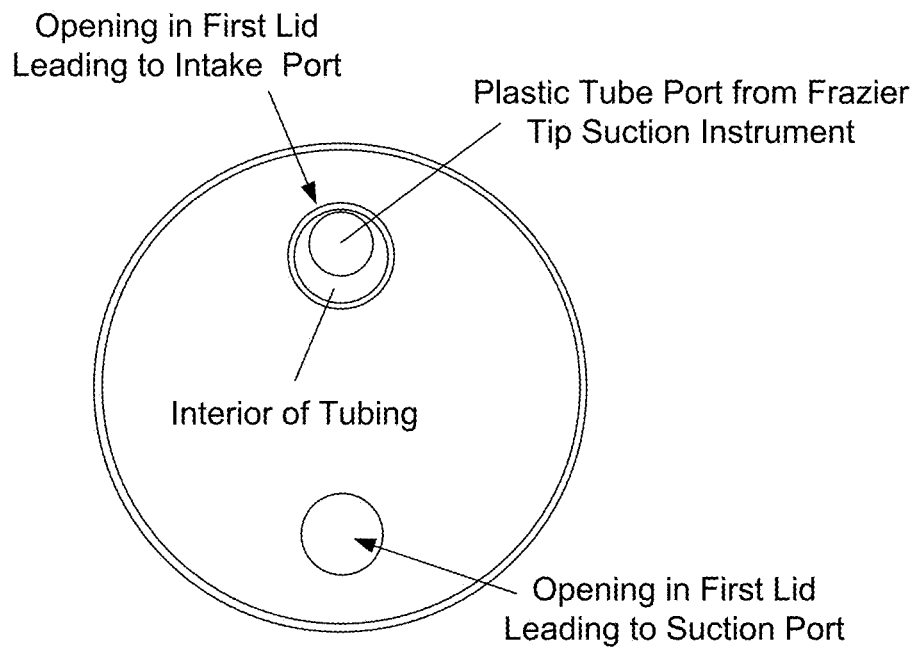
FIG. 11 schematically illustrates, in part, a plan view of the underside of the first lid with a Frazier suction tip instrument attached to the six-inch tubing.
Figure 12:
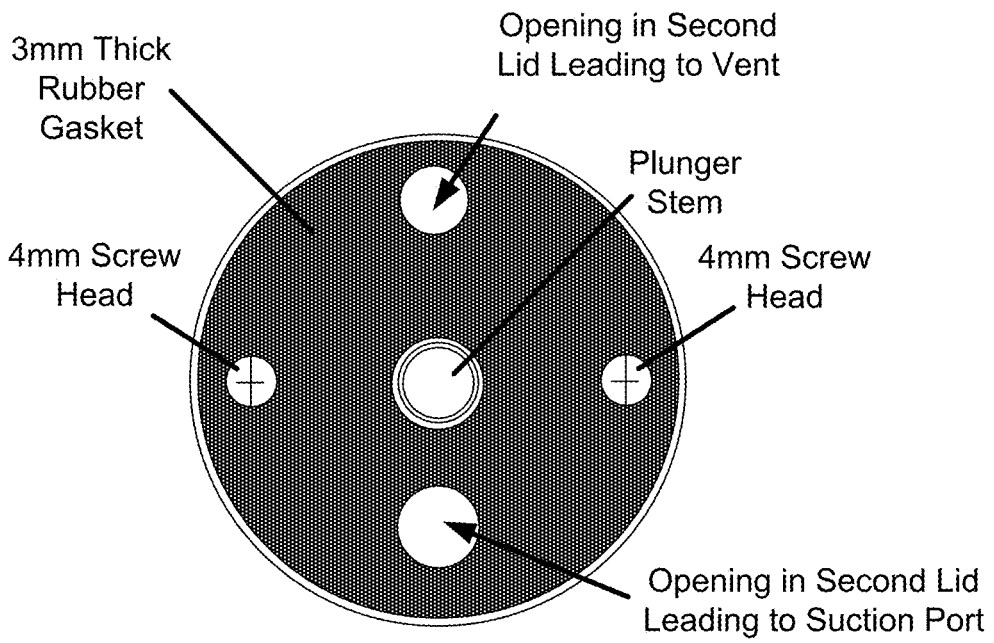
FIG. 12 schematically illustrates, in part, a plan view of the underside of the second lid without the press head.
Figure 13:
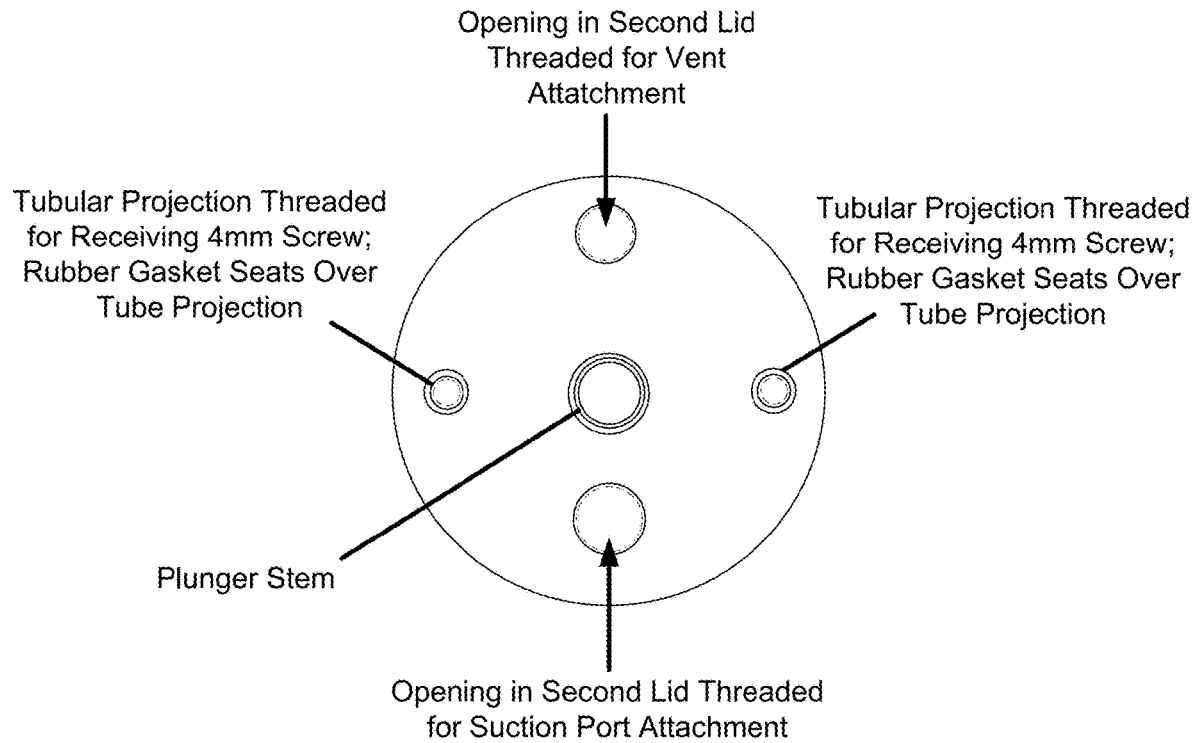
FIG. 13 schematically illustrates, in part, a plan view of the underside of the second lid without the press head, without the 3 mm rubber gasket and screws, without the suction port, and without the intake port.
Figure 14:
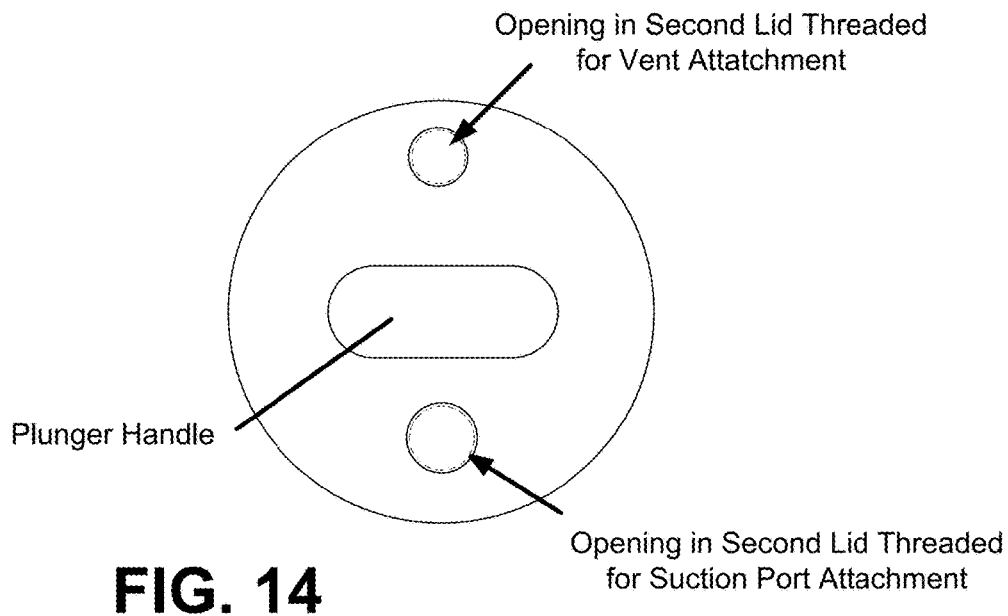
FIG. 14 schematically illustrates, in part, a plan view of a top side of the second lid without the suction port and without the intake port.

With respect to additional details regarding the first lid 102 and second lid 202, FIG. 11 schematically illustrates, in part, a plan view of the underside of the first lid with a Frazier suction tip instrument attached to the tubing; FIG. 12 schematically illustrates, in part, a plan view of the underside of the second lid without the press head, and reveals two 4 mm stainless steel screws with wide heads that collectively retain a 3 mm rubber gasket in place; FIG. 13 schematically illustrates, in part, a plan view of the underside of the second lid without the press head, without the 3 mm rubber gasket and screws, without the suction port, and without the intake port, and reveals two tubular projections threaded for receiving the 4 mm screws and over which tubular projections the rubber gasket seats, and reveals threaded portions in the lid for receiving a suction port attachment and a vent attachment in threading engagement therewith; and FIG. 14 schematically illustrates in part a plan view of a top side of the second lid without the suction port and without the intake port, and reveals a profile of the handle of the plunger for receiving a palm of a hand.

Perceived Highlighted Benefits of Bone Collection Assemblies

As will be appreciated from the foregoing, the bone collection assembly is disposable and cost effective; proficiently collects autologous bone during a surgical operation; and is easy to construct and is simple to use.

Moreover, it is believed that the bone collection assembly is less prone to clogging during use compared to many conventional devices used for autologous bone collection. Furthermore, the chamber of the 50 cc container is much larger than the collection capacity of many conventional devices used for autologous bone collection, and therefore can be used to collect larger amounts of blood and bone at a single time. The can be especially advantageous during a lumbar fusion.

Additionally, it is believed that the bone collection assembly need not be held by a surgeon during the operation. Moreover, use of the plunger to compress the bone and separate the bone from the blood products need not be performed during collection of the bone and blood products. Instead, this can be done after detachment of the first cover following completion of the first phase of collecting the bone and blood products. This separation step can be performed by auxiliary personnel to the surgeon and first assist, such as a surgical tech or other staff.

Still further, it is believed that the collection method has little if any loss of bone and can be used in various operations; that the bone collection assembly will adequately separate blood products from bone; and that the collected bone can be easily measured and utilized in procedures, such as spinal fusions. Indeed, it is believed that the bone collection assembly can be readily utilized by surgeons in multiple specialties and sub-specialties who require the use of autologous bone.

A Currently Preferred Bone Collection Assembly

Figure 15A:
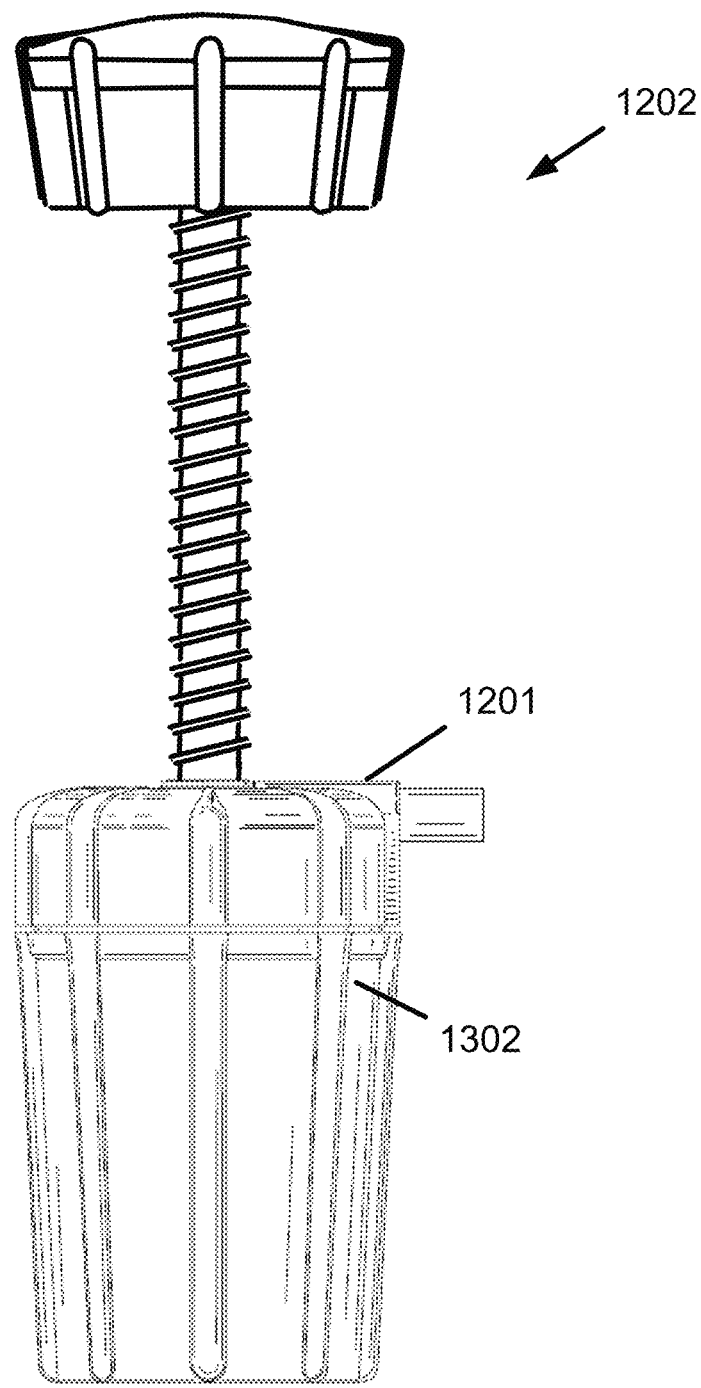
FIG. 15a schematically illustrates another view of the second lid and container of FIG. 15.

A currently preferred bone collection assembly is now described with reference to FIGS. 15-33. In this respect, FIG. 15 schematically illustrates a second lid 1202 attached to a container 1302 of another bone collection assembly in accordance with another embodiment of the present invention. Additionally, FIG. 15a schematically illustrates a side elevational view of the second lid and container of FIG. 15.

As shown in FIG. 15, the second lid 1202 includes a screw-on top 1201 and a plunger assembly. Moreover, while a screw-on engagement is preferred, other engagements are contemplated, such as a snap-fit engagement between lids and a container.

The plunger assembly includes a plunger 1210 that is disposed in a first position as shown in FIG. 15. The plunger 1210 comprises a handle 1212, a shaft 1214, and a press head 1216. The plunger assembly further includes a spring 1215 that is generally coaxial with the shaft 1214 and that extends between the handle 1212 and the top 1201. The spring 1215 biases the plunger 1210 into the first position as shown in FIG. 15, and acts against a downward force A that may be manually applied to the handle 1212 in moving the plunger 1210 from the first position to a second position, in which the press head 1216 is located proximate a bottom of the container 1302.

The screw-on top includes a suction port 1204. In contrast to the suction port 204 of the second lid 202, which extends generally in parallel to the shaft 214 of the plunger 210, the suction port 1204 extends to a side, transversely to the shaft 1214 of the plunger 1210. It is believed that this orientation of the suction port 1204 is beneficial in allowing for deflection of the tubing away from the surgical field of view.

The container 1302 is configured to receive the top 1201 in threading engagement, whereby the top 1201 is screwed onto the container 1302 and can be similarly screwed off of the container 1302. The container 1302 also preferably includes elongate protuberances or ribs 1303 that extend between the top and bottom of the container 1302 along the exterior thereof. The ribs 1303 preferably provide a good gripping surface for holding the container 1302 when screwing the top 1201 onto and off of the container 1302.

Moreover, the top 1201 preferably includes ribs 1203 that also provide a good gripping surface. Furthermore, the ribs 1203 on the top 1201 preferably correspond to and align with the ribs 1303 on the container 1302 when the top 1201 is securely screwed onto the container 1302, thereby readily visually indicating that the top 1201 is tightly screwed onto the container 1302.

FIG. 16 schematically illustrates the detachability of the second lid 1202 and the container 1302.

FIG. 17 schematically illustrates a top plan view of the second lid 1202 detached from the container 1302 as shown in FIG. 16; and FIG. 18 schematically illustrates a side plan view of the second lid 1202 and container 1302 of FIG. 17, including a cross-sectional view of the second lid 1202 taken along the line 18-18 in FIG. 17.

FIG. 19 schematically illustrates a plan view of the bottom of the press head 1216 and illustrates a woven metal mesh disc 1218.

The disc 1218 preferably is secured to the press head 1216 in an injection molding process, with a circumferential portion of the press head 1216 being formed about a circumferential outer portion of the disc 1218 to thereby hold the disc 1218 within a recessed area on the underside of the press head 1216. In this respect, in at least one preferred embodiment, the press head 1216 includes a lip of approximately 0.020 inches. In other embodiments, the disc may be glued or otherwise adhered to the press head, or secured using mechanical fasteners.

Furthermore, the disc 1218 preferably includes four openings through which alignment protuberances or pins 1221 of the press head 1216 extend for alignment of the disc 1218 to the press head 1216.

Additionally, the disc 1218 is supported by the press head as the plunger is moved through any contents in the container from the first position to the second position along the radially extending, elongate areas 1223 as indicated in FIG. 19. These areas comprise an alternating sequence of long and short radially extending, elongate areas 1223 spaced at equal intervals circumferentially about the disc 1218, and correspond to elongate, radially extending support members 1225 on the underside of the press head 1216. This support arrangement provides generally equally distributed support of the disc 1218 during filtration of the bone from the blood while also providing a very large filtration area (as will be appreciated, most of the surface of the disc 1218 actively filters the bone from the blood).

With further regard to the press head 1216 and omitting the disc 1218, FIG. 20 schematically illustrates a side plan view of the press head 1216; FIG. 21 schematically illustrates a top plan view of the press head 1216; and FIG. 22 schematically illustrates a perspective view of the press head 1216.

Figure 23:
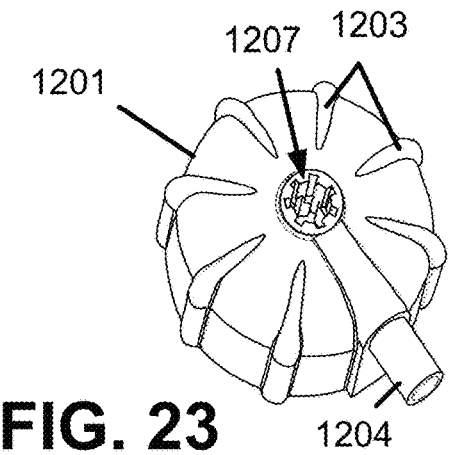
FIG. 23 schematically illustrates a perspective view of a screw-on top of the second lid of FIG. 18.

FIG. 23 schematically illustrates a perspective view of the screw-on top 1201.

Figure 24:
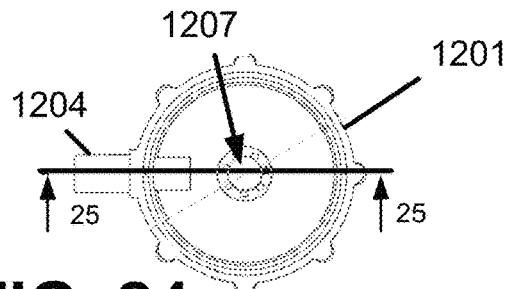
FIG. 24 schematically illustrates a bottom plan view of the screw-on top of FIG. 23.
Figure 25:
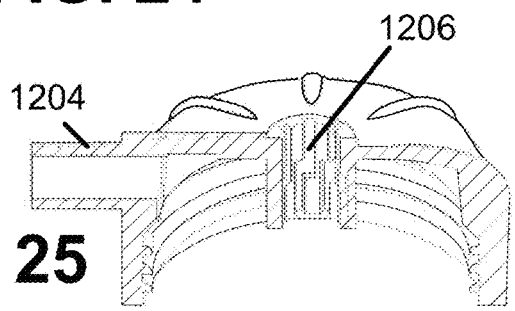
FIG. 25 schematically illustrates a perspective view of a cross-section of the screw-on top of FIG. 23 taken along the line 25-25 in FIG. 24.
Figure 26:
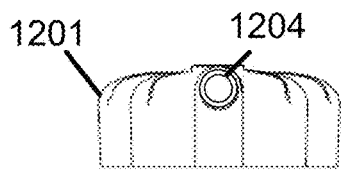
FIG. 26 schematically illustrates a side plan view of the screw-on top of FIG. 23.
Figure 27:
FIG. 27 schematically illustrates another side plan view of the screw-on top of FIG. 23.

FIG. 24 schematically illustrates a bottom plan view of the screw-on top 1201; FIG. 25 schematically illustrates a perspective view of a cross-section of the screw-on top 1201 taken along the line 25-25 in FIG. 24; FIG. 26 schematically illustrates a side plan view of the screw-on top 1201; and FIG. 27 schematically illustrates another side plan view of the screw-on top 1201.

It will be seen from these drawings that the screw-on top 1201 defines passageways 1206 formed in the axial extent of the opening 1207 in the top 1201 through which the shaft 1214 of the plunger 1210 is received. These passageways 1206 form vents when the shaft 1214 is received though the opening 1207 and perform the same function as vent 206 in the cover 202 described above.

Furthermore, each passageway 1206 includes a top portion that is generally oriented in parallel to the axis of the opening 1207 and shaft 1214 when received therethrough; a middle portion that is generally circumferentially oriented to the axis of the opening 1207 and shaft 1214 when received therethrough; and a bottom portion that is generally oriented in parallel to the axis of the opening 1207 and shaft 1214 when received therethrough. The top portion and bottom portion of each passageway 1206 are thus offset from each other along the circumferential direction about the opening 1207. This is perhaps best seen in the passageway 1206 called out in FIG. 25.

Figure 28:
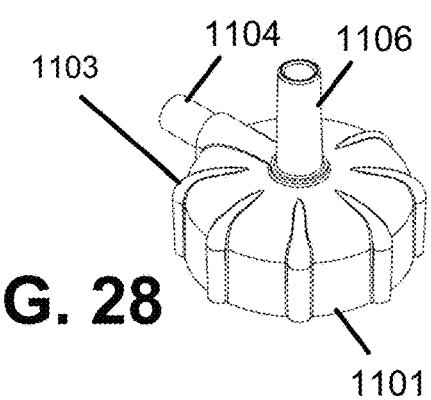
FIG. 28 schematically illustrates a perspective view of a screw-on top of a first lid for use with the container of FIG. 15.
Figure 29:
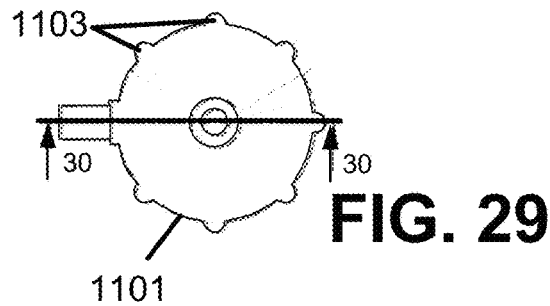
FIG. 29 schematically illustrates a bottom plan view of the screw-on top of FIG. 28.
Figure 30:
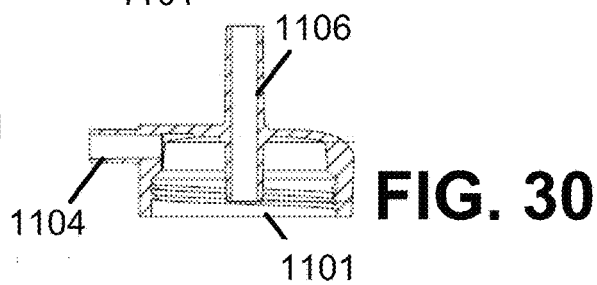
FIG. 30 schematically illustrates a cross-sectional view of the screw-on top of FIG. 28 taken along the line 30-30 in FIG. 29.
Figure 31:
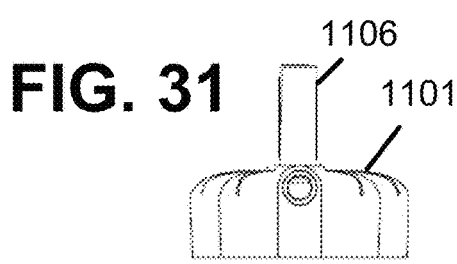
FIG. 31 schematically illustrates a side plan view of the screw-on top of FIG. 28.
Figure 32:
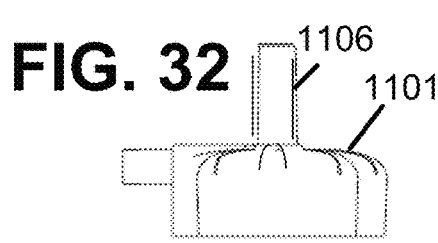
FIG. 32 schematically illustrates another side plan view of the screw-on top of FIG. 28.

FIG. 28 schematically illustrates a perspective view of a screw-on top 1101 of a first lid for use with the container 1302 of FIG. 15; FIG. 29 schematically illustrates a bottom plan view of the screw-on top 1101; FIG. 30 schematically illustrates a cross-sectional view of the screw-on top 1101 taken along the line 30-30 in FIG. 29; FIG. 31 schematically illustrates a side plan view of the screw-on top 1101; and FIG. 32 schematically illustrates another side plan view of the screw-on top 1101. As seen in these drawings, the screw-on top 1101 includes a suction port 1104 and an intake port 1106. Ribs 1103 are also provided and function in the same manner as ribs 1203.

As will be appreciated from the foregoing description and drawings, a bone collection assembly in accordance with one or more aspects of the invention is used to efficiently and effectively collect bone particles, bone fragments, blood and other products created during intraoperative bone removal. The bone collection assembly separates the bone from these other materials into a desirable autologous graft for use during bone fusion procedures. The compressed bone obtained from using the bone collection assembly can be contoured into virtually any shape dictated by surgical needs, whether it be on-lay grafting or interbody fusion. It is believed that the compressed bone is viable and can be safely delivered back to the patient, decreasing the surgical team's reliance on expensive synthetics, allograft and remote bone harvesting.

Figure 33A:
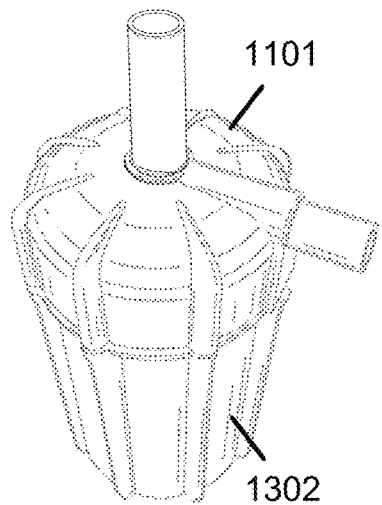
FIG. 33a schematically illustrates a perspective view of the lid of FIGS. 28-32 attached to a container of a bone collection assembly in accordance with a preferred embodiment of the present invention.
Figure 33B:
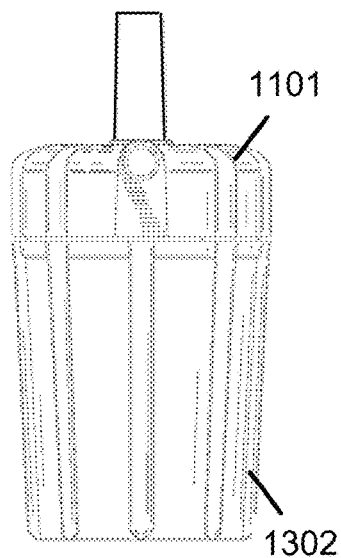
Figure 33C:
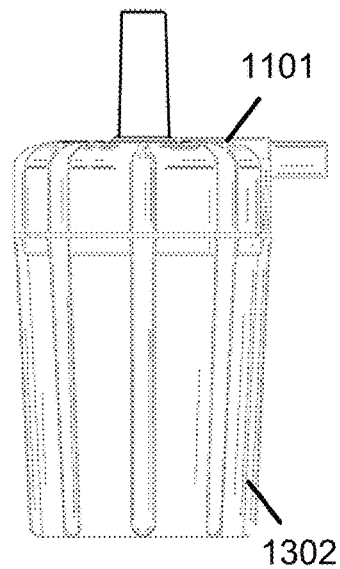
Figure 33F:
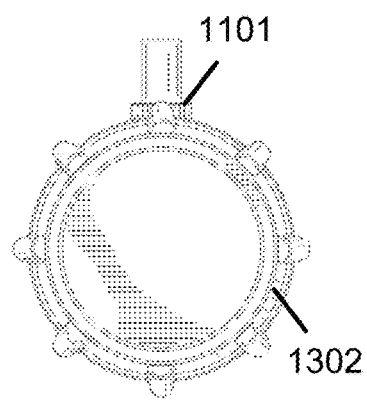
Figure 33D:
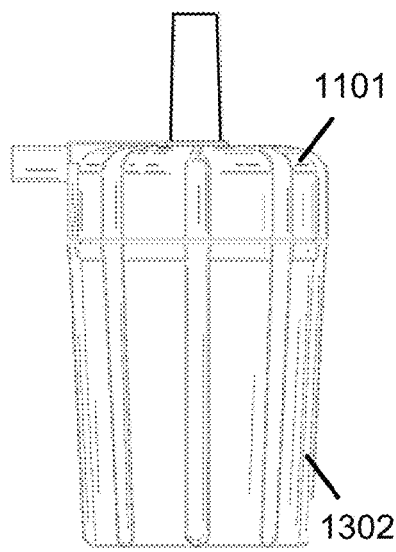
Figure 33E:
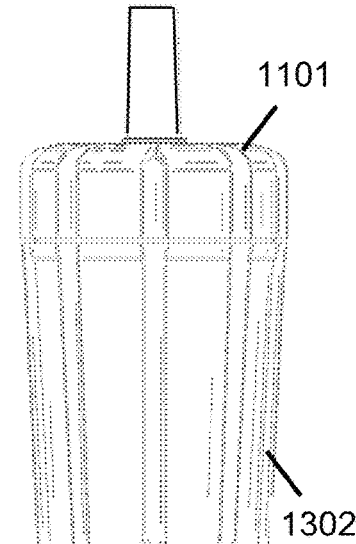
Figure 33G:
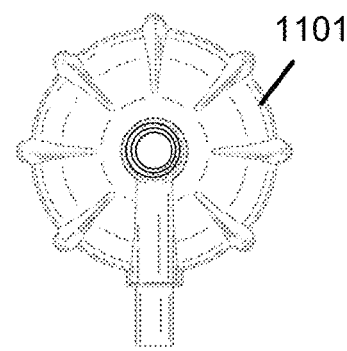

With regard now to FIGS. 33*a*-33*g*, FIG. 33*a* schematically illustrates a perspective view of the screw-on top 1101 of FIGS. 28-32 attached to container 1302. Additionally, FIG. 33*b* schematically illustrates a front elevational view of the screw-on top 1101 attached to container 1302; FIG. 33*c* schematically illustrates a side elevational view of the screw-on top 1101 attached to container 1302; FIG. 33*d* schematically illustrates another side elevational view of the screw-on top 1101 attached to container 1302; FIG. 33*e* schematically illustrates a rear elevational view of the screw-on top 1101 attached to container 1302; FIG. 33*f* schematically illustrates a bottom plan view of the screw-on top 1101 attached to container 1302; and FIG. 33*g* schematically illustrates a top plan view of the screw-on top 1101 attached to container 1302.

Figure 34A:
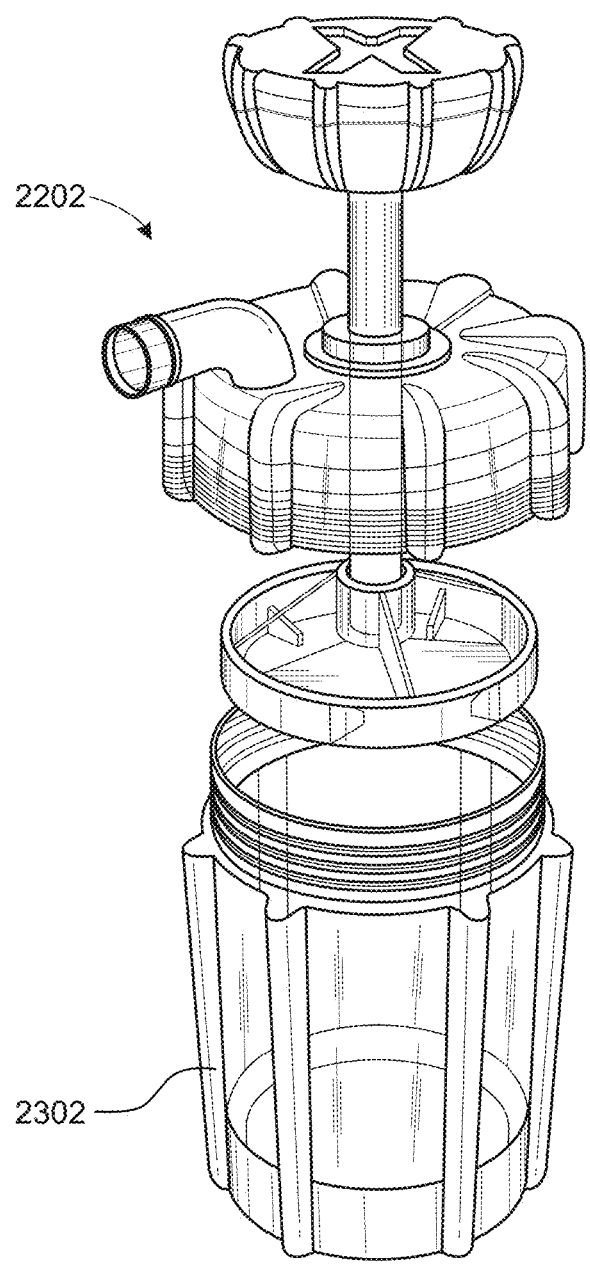
FIG. 34a is a perspective view of a container and cover with plunger assembly in accordance with another preferred embodiment of the present invention.
Figure 34B:
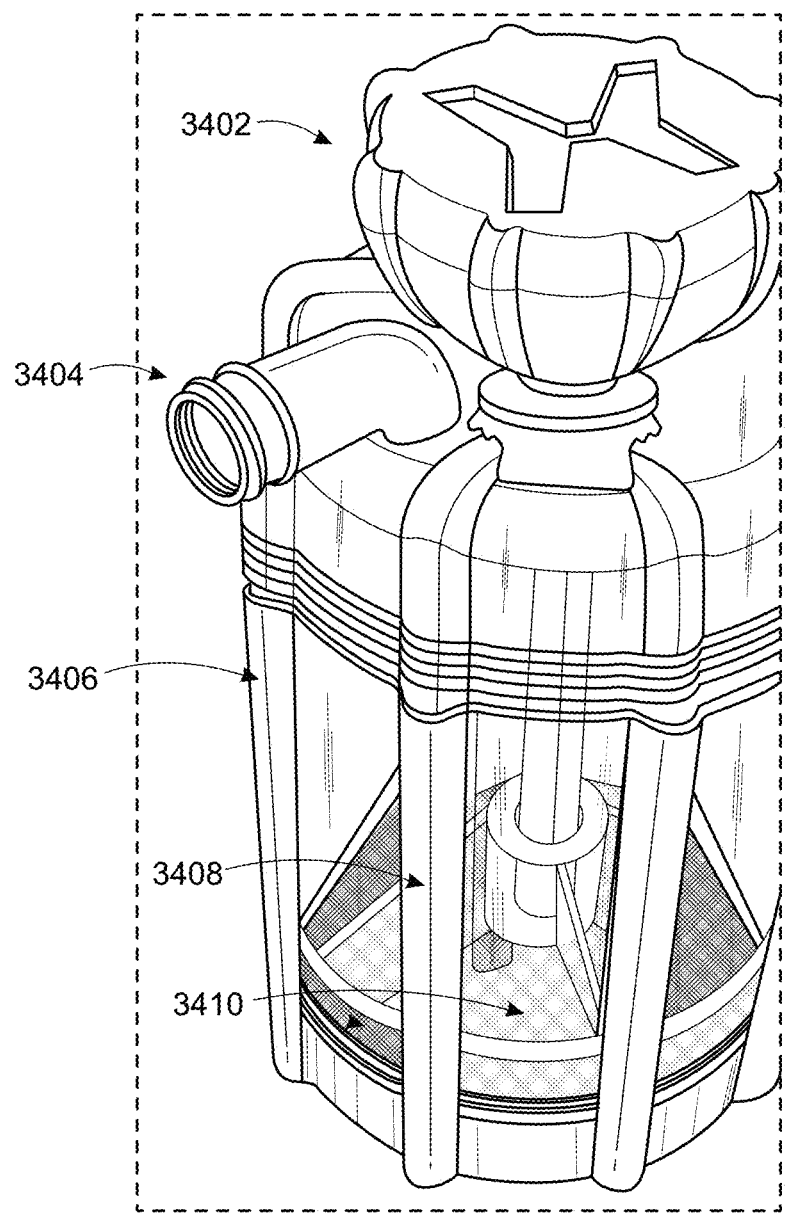

FIG. 34*a* is a partially exploded perspective illustration of a container 2302 and cover 2202 of a preferred commercial embodiment in accordance with one or more aspects of the present invention. FIG. 34*b* is another perspective view of the container and cover of FIG. 34*a*, but shown with cover 2202 and container 2302 attached. With reference to FIG. 34*b*, it is believed that the top generally indicated at 3402 is ergonomically designed to enhance ease of use; the suction port generally indicated at 3404 is strategically positioned to prevent suction tubing from interfering with surgical field of view; the translucent collection chamber generally indicated at 3406 allows for direct visualization of contents collected in the container; external ribs, one of which is generally indicated at 3408, align with ridges on the top and insure proper assembly of the device; and press head with surgical grade mesh generally indicated at 3410 maximizes separation of autologous bone from blood.

Additional Context of Use

While the description of preferred embodiments of the invention have been in the context of collection of bone during surgical procedures, another context of use comprises use of one or more such collection assemblies, methods, and systems in the collection of tissue during surgical procedures and, in particular, for the collection of tissue as it is removed from the body utilizing ultrasonic tissue evacuation devices. The primary function would be not only to collect all material removed from the body with, for example, an ultrasonic tissue evacuator, but also to separate the target tissue (tumor bone and other tissues) from body fluids and irrigation fluids. Such fluids could include blood; saline; and irrigant—which is delivered through the aspiration site, for example, by ultrasonic tissue evacuators.

For example, one or more embodiments of the invention can be utilized during tumor collection with surgical aspirators such as the CUSA ultrasonic surgical aspirator commercially available from Integra Lifesciences, which is a suction, irrigation and ultrasonic device widely used for removal of abnormal tissue, such as brain and liver tumors. Ultrasonic tissue evacuation devices have been used since the late 1970s. These devices have a multitude of uses, and each generally comprises a hand piece which is used like a wand. It is held in a surgeon's hand and the tip of this apparatus is used not only to break up target tissue with ultrasonic waves, but also to deliver irrigant and suction to the tip allowing removal of the target tissue. The tissue once freed from the body is removed via tubing to a vacuum system. This vacuum system is commonly that of the suction supply present in virtually all operating rooms. Keeping as much as possible of the tissue that is removed is very important. Thus, while in transit through the suction tubing, tissue that is removed is suctioned from the surgical site, with the irrigation fluid and body fluid, away from the sterile field into and through a canister that includes a semipermeable sock to catch and filter out the tissue from the fluid. Unfortunately, the sock is non-sterile and is ineffective in condensing the tissue and removing the fluids; consequently, a slurry of material captured by the sock—comprising primarily clotted blood—is sent to the pathologist for tissue analysis. The methodology of using the sock for collection contaminates the tissue, too.

In accordance with one or more aspects of the invention, embodiments of the collection system of the present invention are used to capture the removed tissue that is cut and suctioned through the tubing, and the non-sterile cloth sock preferably is not used. It is believed that this enables a surgeon to collect nearly all of the tissue that is removed in a sterile manner free from most of the fluids that are also removed with the tissue. A preferred method and a preferred collection assembly in this context of use will now be described in detail.

Figure 35:
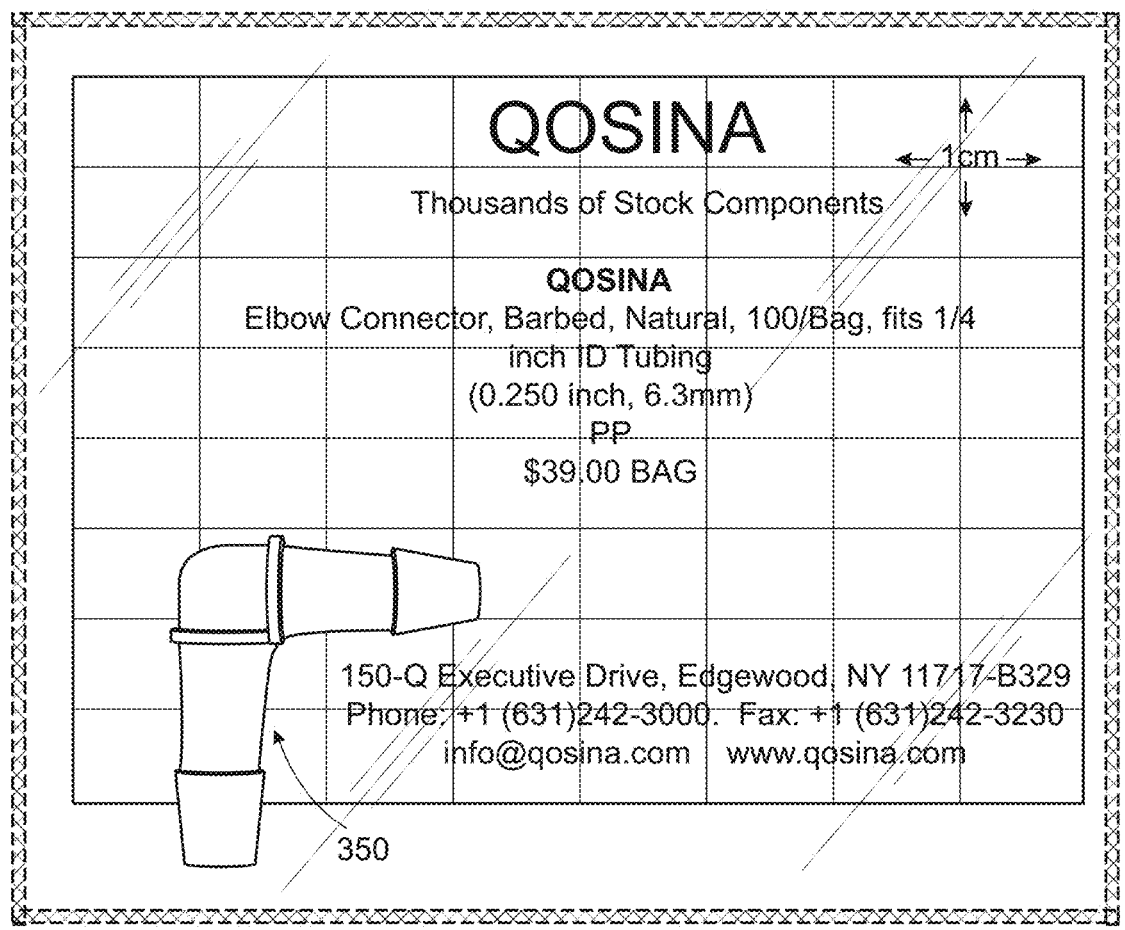
FIG. 35 illustrates an elbow connector that is used in the collection assembly of FIGS. 38a-38i.

An ultrasonic device is attached and set up in its usual fashion. A preferred collection assembly kit in accordance with one or more aspects of the invention is opened at the beginning of the case and placed on the surgical table. The kit preferably comprises any of the kits disclosed herein in the context of bone collection (including two collection containers), and further preferably includes an elbow connector such as, for example, the right-angle elbow connector 350 illustrated in FIG. 35. The elbow connector preferably has a quarter-inch inner diameter, is made from polypropylene, and is sterile. The elbow connector is used to join the silicon tubing extending from the collection top with tubing from the ultrasonic device, helps to maintain a steady flow of suction to the ultrasonic device, and allows suctioned contents from the ultrasonic tool to fall into the container.

Figure 36:
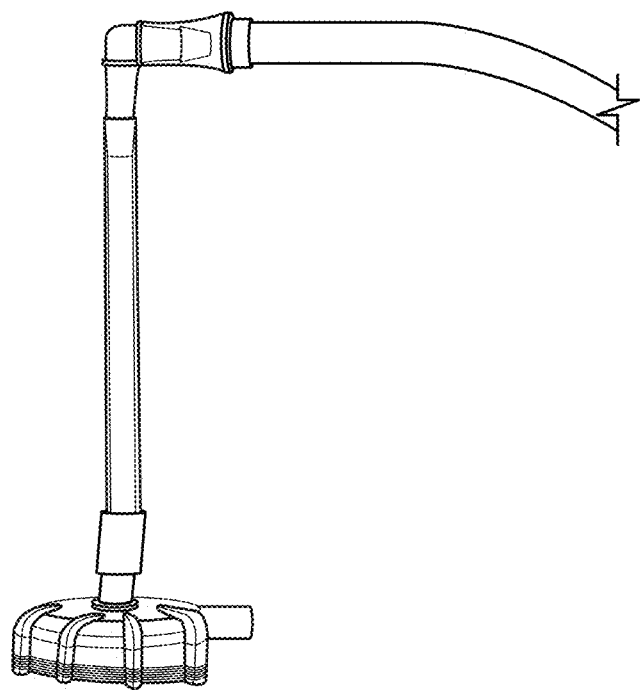
FIG. 36 illustrates a prototype of the first screw-on top in the collection assembly of FIGS. 38a-38i, together with a suction tube that has been attached to the elbow connector.
Figure 37:
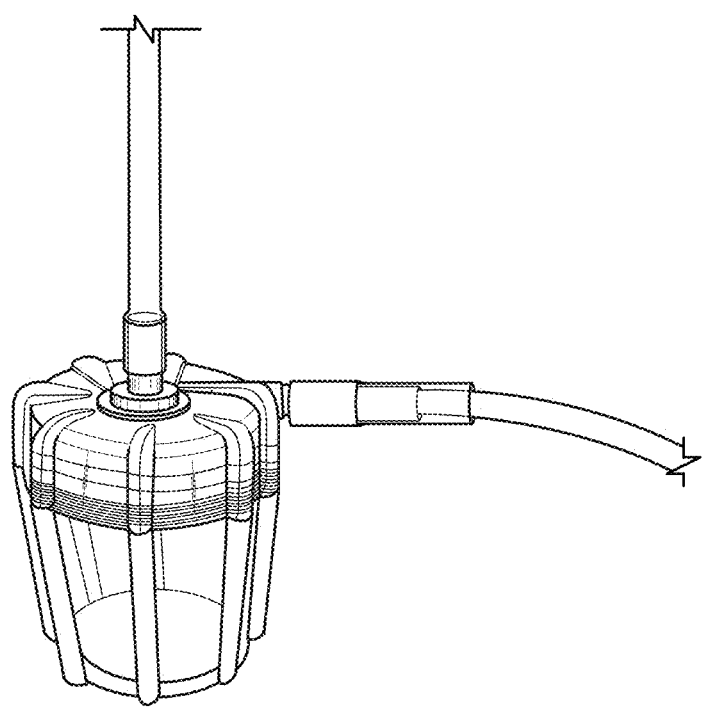
FIG. 37 illustrates a container and the first screw-on in the collection assembly of FIGS. 35a-35i, wherein the screw-on top has been secured on top of the container and the tubing from an ultrasonic device has been attached to the side port of the screw-on top.

The second container top with the plunger and one of the collection containers of the kit are removed from the sterile kit packaging and placed, unattached to each other, on the sterile surgical table. The first container top and the sterile elbow connector provided in the kit are removed, and the elbow connector is attached to the silicon tubing projecting superiorly from the first container top (this arrangement is illustrated in FIG. 36). The other container provided in the kit and the first container top are screwed together and the suction tubing for the suction source provided in the operating room is attached to the elbow connector of the first container top. The surgical tubing provided in the operating room is then run off the patient lengthwise and attached to the operating room provided suction source. The tubing from the ultrasonic device is attached to the side port of the first container top. The container with the first collection top is then ready for use in collecting tissue and fluid removed via the ultrasonic device.

During use, the container with the first collection top is secured to the side of the patient between the assistant and the tech and left there. The surgical drape is folded over the elbow and remains there until the case is complete.

Once the first container is filled with blood and biological tissue, the ultrasonic portion of the case is halted momentarily. Preferably, the first assistant unscrews the filled container and passes it to a tech, who is present in the operating room. The tech accepts the filled container, while handing back to the assistant the second empty container staged on the surgical table. The second empty container is screwed onto the first collection top and the procedure resumes. Preferably, this exchange takes approximately 10-15 seconds.

As the surgery continues, the tech screws the second container top that includes the plunger onto the filled container of blood, irrigation and pathology. Additional suction tubing, provided by the operating room, is attached to the side port of the second container top, and the plunger thereof is manually deployed downward with gentle, steady pressure. Once the press head has reached the bottom of the container, the container is tilted and the fluid is suctioned away. After the fluid contents have been evacuated, the top is brought back up to its resting position, which is assisted by a spring incorporated into the plunger assembly. The container then is unscrewed and the pathology is placed onto a non-absorbable pad, such as a telfa pad. The second container top with plunger, and the empty container, then are placed back onto the surgical table and used again thereafter to repeat this process for collecting as much tissue as possible.

As will be appreciated, once the collection container is attached and staged and the case begins, the collection process principally comprises swapping and pressing thereafter until the case is completed.

Once the case is complete, the collection apparatus is discarded in accordance with HAZMAT disposal procedures of the respective hospital.

Figure 38A:
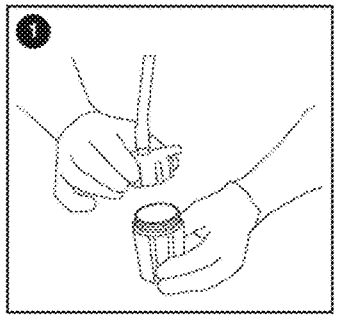
FIGS. 38a-38i schematically illustrate another use of a collection assembly in accordance with another preferred embodiment of the present invention, wherein tissue is collected in connection with the user of an ultrasonic tool.

Illustrations representative of instructions for use that are preferably included in a kit for collection of tissue in such operations are illustrated in FIGS. 38a-38i. In accordance with these illustrations, the following is representative of written instructions that would be provided, which are illustrative of the foregoing description of use:

FIG. 38a—Step 1: Attach collection top, with silicone tubing extending from top port, to an empty container so that ribs align.

Figure 38B:
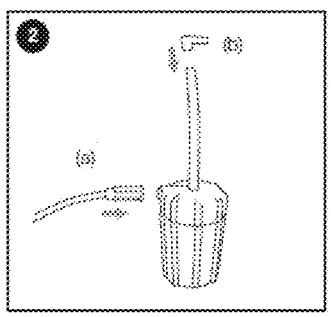

FIG. 38b—Step 2: Attach the ultrasonic device's evacuation tubing to side port (a). Attach provided elbow connector to silicon tubing (b). Ensure connections are well seated.

Figure 38C:
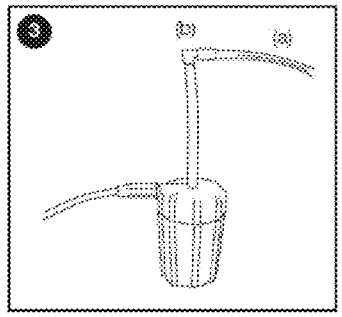

FIG. 38c—Step 3: Attach the operating room provided suction tubing (a) to elbow connector (b). Ensure connection is well seated.

Figure 38D:
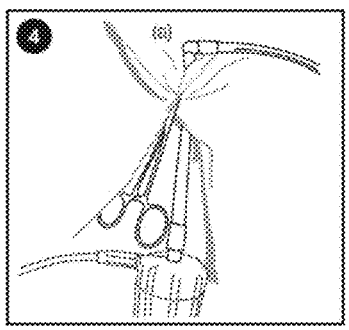

FIG. 38d—Step 4: Secure the collection container to the patient's sterile drape on the side of the patient by folding the drape over the elbow (a). Secure with operating room provided snap, Kocher or forcep instrument. Attachment of first container top is maintained during the case.

Figure 38E:
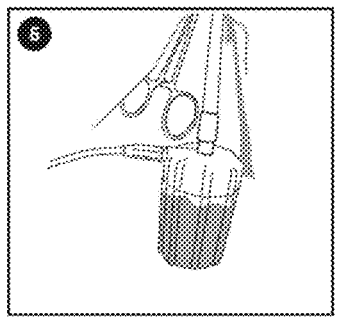

FIG. 38e—Step 5: Once collection container is almost full, halt operating of ultrasonic device.

Figure 38F:
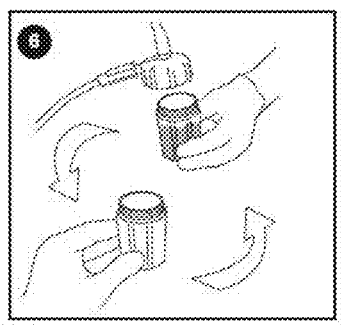

FIG. 38f—Step 6: Unscrew the collection container and replace the collection container with the other, empty collection container. Pass filled collection container to tech. Once empty collection container is securely attached to the first collection top, resume operating of ultrasonic device.

Figure 38G:
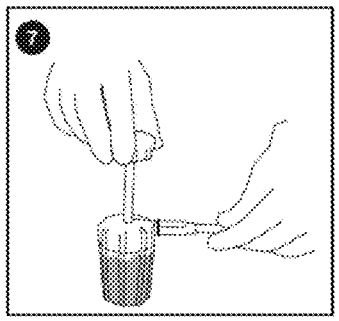

FIG. 38g—Step 7: Attach press top to filled collection container. Align ribs. Attach suction to side port and manually depress plunger. *Ensure suction is operational *Filled container can be hand-held or placed on the Mayo table.

Figure 38H:
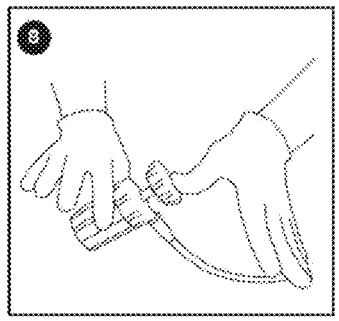

FIG. 38h—Step 8: Once fully depressed, tilt collection container to evacuate fluid through side port via suction. Repeat if needed.

Figure 38I:
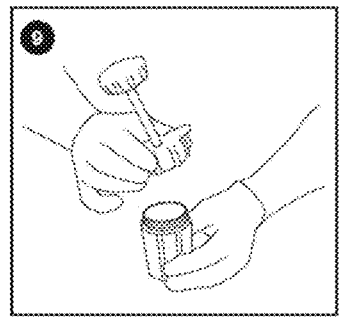

FIG. 38i—Step 9: Unscrew and remove press top from collection container. Remove biologic material and stage on sterile pad, such as telfa pad. Tissue can be sent to pathology or staged to be used as surgeon desires. *Recommend using a Periosteal instrument.* Repeat steps 5-9 until surgery is complete.

The use of a collection assembly kit in accordance with one or more aspects of the invention addresses at least two flaws now recognized with the current "sock" technology used with ultrasonic devices. Specifically, collection now occurs in accordance with preferred embodiments of the invention on the sterile field of surgery and the issue of contamination of the tissue is avoided. This would enable, for example, cultures to be obtained from the tissue. In contrast, if cultures had been attempted utilizing the current sock technology, contamination would be a serious concern.

Secondly, the tissue in accordance with preferred embodiments of the invention is able to be compressed, removing the vast majority of unwanted fluids prior to submitting the tissue for analysis. This is believed to be of significant benefit to pathology, in that the tissue submitted for study would be largely that of the pathology and not diluted by saline irrigant and clotted blood. This could result in a significant cost savings in that time previously wasted attempting to isolate representative tissue would no longer be necessary. The tissue specimen would be much more representative of the pathology.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method of collecting bone from a liquid using an apparatus, comprising:
   (a) suctioning liquid containing bone into a containment area of a container of the apparatus;
   and after performing said step (a),
   (b) suctioning liquid from the container;
   (c) manually compressing the bone by moving a press head of a plunger of the apparatus from an initial position proximate an underside of a lid attached to the container in a direction toward the bottom of the containment area; and
   (d) spring biasing the press head toward the initial position using a spring that is located along a shaft extending from a handle of the plunger through an opening in the lid to the press head, the spring being located on the shaft between the handle and the lid, the apparatus being configured such that the spring biases the press head into the initial position proximate the underside of the lid absent manual application of force to the handle of the plunger;
   (e) wherein the step of manually compressing the bone comprises manually pushing the handle of the plunger toward the lid in opposition to the spring biasing of the press head; and
   after performing said steps (b) through (d),
   (f) opening the container by detaching the lid from the container; and
   (g) withdrawing the collected and compressed bone from the container.

2. The method of claim 1, further comprising holding the container while both manually compressing the bone and suctioning liquid from the container.

3. The method of claim 1, wherein the plunger is retained on the lid.

4. The method of claim 1, wherein the spring is coaxial with the shaft.

5. The method of claim 1, wherein the container comprises a threaded rim, and wherein the lid is detachable from the container by manually unscrewing the lid and the container.

6. The method of claim 5, wherein the lid comprises exterior ribs providing a gripping area for manually unscrewing the lid and the container.

7. The method of claim 1, wherein the container comprises a cylindrical container having a single, open end comprising a mouth of the container.

8. The method of claim 7, wherein the container comprises a threaded rim, and wherein the lid is configured to be screwed onto the container in sealing engagement with the mouth of the container.

9. The method of claim 1, wherein compressing the bone forces liquid from the compressed bone thereby filtering bone from the liquid.

10. The method of claim 1, wherein compressing comprises compressing the bone against a screen of the apparatus.

11. The method of claim 1, further comprising venting the container while compressing and drawing off fluid from the container.

12. The method of claim 11, wherein the venting comprises suctioning air from an exterior of the container into the container.

13. The method of claim 12, wherein the suctioning of air from an exterior of the container into the container occurs at the location at which the shaft extends through the lid.

14. The method of claim 1, wherein suctioning liquid from the container comprises connecting the container to a suction source using a tube.

15. The method of claim 1, wherein suctioning liquid containing bone into the container comprises suctioning the liquid containing the bone from a surgical site using a medical instrument.

16. The method of claim 15, wherein the medical instrument comprises an ultrasonic device for cutting and removing tissue.

17. The method of claim 1, wherein the apparatus further comprises a suction port configured for attachment of an end of a tube for suctioning liquid from the container.

18. The method of claim 17, wherein the suction port extends in a radial direction away from an axis of the cylindrical container.

19. A method of collecting bone from a liquid using an apparatus, comprising:
   (a) suctioning liquid containing bone into a containment area of a container of the apparatus;
   and after performing said step (a),
   (b) suctioning liquid from the container via a suction tube secured to a suction port of the apparatus;
   (c) manually compressing the bone against a screen of the apparatus by moving a press head of a plunger of the apparatus from an initial position proximate an underside of a lid attached to the container in a direction toward the bottom of the containment area such that the screen filters bone from liquid by allowing liquid to pass through the screen but not allowing the manually compressed bone to pass through the screen; and
   (d) spring biasing the press head toward the initial position using a spring that is located along a shaft extending from a handle of the plunger through an opening in the lid to the press head, the spring being located on the shaft between the handle and the lid, the apparatus being configured such that the spring biases the press head into the initial position proximate the underside of the lid absent manual application of force to the handle of the plunger;
   (e) wherein the step of manually compressing the bone comprises manually pushing the handle of the plunger toward the lid in opposition to the spring biasing of the press head; and
   (f) wherein, while suction is being applied via the suction tube secured to the suction port, when the press head is in the initial position, the suction port is located downflow of the screen such that the screen prevents bone from being suctioned out; and
   after performing said steps (b) through (d),
   (g) opening the container by detaching the lid from the container; and
   (h) withdrawing the collected and compressed bone from the container.

20. A method of collecting bone from a liquid using an apparatus, comprising:
   (a) suctioning liquid containing bone into a containment area of a container of the apparatus, the container comprising a cylindrical container having a first open end representing a mouth of the container and a second closed end opposite the first open end;
   and after performing said step (a),
   (b) suctioning liquid from the container via a suction tube secured to a suction port of the apparatus;
   (c) manually compressing the bone against a screen of the apparatus by moving a press head of a plunger of the apparatus from an initial position proximate an underside of a lid attached to the container in a direction toward the bottom of the containment area such that the screen filters bone from liquid by allowing liquid to pass through the screen but not allowing the manually compressed bone to pass through the screen, the lid being secured to the mouth of the container via threaded engagement with a threaded rim surrounding the mouth of the container; and
   (d) spring biasing the press head toward the initial position using a spring that is located along a shaft extending from a handle of the plunger through an opening in the lid to the press head, the spring being located on the shaft between the handle and the lid, the apparatus being configured such that the spring biases the press head into the initial position proximate the underside of the lid absent manual application of force to the handle of the plunger;
   (e) wherein the step of manually compressing the bone comprises manually pushing the handle of the plunger toward the lid in opposition to the spring biasing of the press head; and
   (f) wherein, while suction is being applied via the suction tube secured to the suction port, when the press head is in the initial position, the suction port is located downflow of the screen such that the screen prevents bone from being suctioned out; and
   after performing said steps (b) through (d),
   (g) opening the container by detaching the lid from the mouth of the container; and
   (h) withdrawing the collected and compressed bone from the container through the mouth of the container to which the lid including the plunger and press head was secured.

* * * * *